US010561466B2

(12) United States Patent
Hedblom et al.

(10) Patent No.: US 10,561,466 B2
(45) Date of Patent: Feb. 18, 2020

(54) AUTOMATED PLANNING SYSTEMS FOR PEDICLE SCREW PLACEMENT AND RELATED METHODS

(71) Applicant: Sectra AB, Linköping (SE)

(72) Inventors: Anders Hedblom, Linköping (SE); Rolf Scheiderbauer, Linköping (SE); Stefan Lindholm, Linköping (SE); Ludvig Mangs, Linköping (SE)

(73) Assignee: Sectra AB, Linköping (SE)

(*) Notice: Subject to any disclaimer, the term of this patent is extended or adjusted under 35 U.S.C. 154(b) by 12 days.

(21) Appl. No.: 16/046,181

(22) Filed: Jul. 26, 2018

(65) Prior Publication Data
US 2019/0046269 A1 Feb. 14, 2019

Related U.S. Application Data

(60) Provisional application No. 62/543,738, filed on Aug. 10, 2017.

(51) Int. Cl.
A61B 34/10 (2016.01)
A61B 34/00 (2016.01)
G06T 15/06 (2011.01)
G06T 7/73 (2017.01)
G06T 19/20 (2011.01)
G06T 7/62 (2017.01)
G06T 7/00 (2017.01)

(52) U.S. Cl.
CPC .............. A61B 34/10 (2016.02); A61B 34/25 (2016.02); G06T 7/0012 (2013.01); G06T 7/62 (2017.01); G06T 7/75 (2017.01); G06T 15/06 (2013.01); G06T 19/20 (2013.01); A61B 2034/104 (2016.02); A61B 2034/105 (2016.02); G06T 2200/24 (2013.01); G06T 2207/10028 (2013.01); G06T 2207/10081 (2013.01); G06T 2207/10088 (2013.01); G06T 2207/30012 (2013.01); G06T 2210/21 (2013.01); G06T 2210/41 (2013.01); G06T 2219/2004 (2013.01); G06T 2219/2016 (2013.01)

(58) Field of Classification Search
None
See application file for complete search history.

(56) References Cited

U.S. PATENT DOCUMENTS

| 7,235,076 | B2  | 6/2007 | Pacheco |              |
|-----------|-----|--------|---------|--------------|
| 2008/0177203 | A1* | 7/2008 | von Jako | A61B 90/36 |
|           |     |        |         | 600/587      |
| 2016/0275703 | A1* | 9/2016 | Mariampillai | A61B 6/03 |

(Continued)

OTHER PUBLICATIONS

"Automated determination of pedicle morphometry in the thoracic spine", by Dejan Knez, Bostjan Likar, Franjo Pernus & Tomaz Vrtovec, 2016 IEEE 13th International Symposium on Biomedical Imaging (ISBI), Apr. 13-16, 2016, pp. 664-667. (Year: 2016).*

(Continued)

Primary Examiner — James A Thompson
(74) Attorney, Agent, or Firm — Myers Bigel, P.A.

(57) ABSTRACT

Systems, methods and circuits can perform automated pedicle placement planning on 3D image data sets of the spine using global and local coordinate axes systems and ray casting to identify a center of the vertebral foramen and a center of a solid vertebral body for the local coordinate axis system.

22 Claims, 17 Drawing Sheets
(14 of 17 Drawing Sheet(s) Filed in Color)

(56) References Cited

U.S. PATENT DOCUMENTS

2017/0112575 A1* 4/2017 Li .................... A61B 34/10
2019/0029757 A1* 1/2019 Roh .................... G06T 19/006

OTHER PUBLICATIONS

"Computer-Assisted Screw Size and Insertion Trajectory Planning for Pedicle Screw Placement Surgery", by Dejan Knez, Bostjan Likar, Franjo Pernus & Tomaz Vrtovec, IEEE Transactions on Medical Imaging, vol. 35, No. 6, pp. 1420-1430, Jun. 2016. (Year: 2016).*

Dodin et al. "A fully automated human knee 3D MRI bone segmentation using the ray casting technique" Medical & Biological Engineering & Computing, 49:1413-1424 (2011).

Goerres et al. "Atlas-based pedicle trajectory prediction for automatic assessment and guidance of screw insertions" http://istar.jhu.edu/pdf/CARS2016_Goerres_PedicleTrajectoryPrediction.pdf (5 pages) (2016).

Knez et al. "Computer-Assisted Screw Size and Insertion Trajectory Planning for Pedicle Screw Placement Surgery" IEEE Transactions on Medical Imaging, 35(6):1420-1430 (2016).

Kronman et al. "Anatomical structures segmentation by spherical 3D ray casting and gradient domain editing" Medical Image Computing and Computer-Assisted Intervention, 15(Pt 2):363-370 (2012).

Lee et al. "Automated Surgical Planning and Evaluation Algorithm for Spinal Fusion Surgery with Three-Dimensional Pedicle Model" (pp. 2524-2531) IEEE/RSJ International Conference on Intelligent Robots and Systems, Sep. 25-30, 2011.

Lukacs et al. "Faithful Least-Squares Fitting of Spheres, Cylinders, Cones and Tori for Reliable Segmentation" European Conference on Computer Vision, pp. 671-686 (1998).

mediCAD "Pedicle Screws and Implants" Product Description: https://www.hectec.de/content/index.php/us/template/medicad-spine-3d/pedicle-screws-implants (2 pages) (2013).

Mohar et al. "Comparison of Automatically Manually Obtained Pedicle Screw Plans in Deformities of the Thoracic Spine" (24 pages) ISTA Boston, Oct. 5-8, 2016.

Naddeo et al. "An automatic and patient-specific algorithm to design the optimal insertion direction of pedicle screws for spine surgery templates" Medical & Biological Engineering & Computing, 55(9):1549-1562 (2017).

Wicker et al. "Automatic Determination of Pedicle Screw Size, Length, and Trajectory from Patient Data" (4 pages) Proceedings of the 26th Annual International Conference of the IEEE EMBS, Sep. 1-5, 2004.

Xiaozhao et al. "A method of lumbar pedicle screw placement optimization applied to guidance techniques" Computer Assisted Surgery, 21(51):143-148 (2016).

* cited by examiner

AUTOMATED PLANNING SYSTEMS FOR PEDICLE SCREW PLACEMENT AND RELATED METHODS

RELATED APPLICATIONS

This application claims the benefit of and priority to U.S. Provisional Patent Application Ser. No. 62/543,738, filed Aug. 10, 2017, the content of which is hereby incorporated by reference as if recited in full herein.

FIELD OF THE INVENTION

The invention relates to automated planning guidance for proper pedicle screw placement associated with three dimensional (volumetric) image data sets of the spine.

BACKGROUND

Pedicle screws are often used for spinal procedures such as when doing spine arthrodesis—to fuse several vertebrae into one rigid body—or when straightening out a pathologically bent spine. The insertion of pedicle screws is a procedure that requires delicate precision. That is, pedicle screw placement should be carried out precisely in target bone and the first step to success is good planning. A well-structured and precise surgical plan can contribute to a successful surgery in several ways, such as: saving time during surgery, which in turn reduces the risk of infection and allowing shorter operation time and reduce any subsequent operation which can decrease costs. Done properly, planning can also provide information to surgeons so that viable approaches are identified before they are physically tried. This reduces the number of preventable mistakes, had the surgeons had more information of the situation. Also, planning can give information about which tools and implants are needed and exact lengths and diameters for screws can be determined in advance.

In the past, manual insertion has been used, where the screws are completely adjusted by a surgeon/user to fit the pedicles. This is a very time consuming approach. Manually planning the placement of every single pedicle screw in 3D can be very tedious, particularly where multiple screws are to be inserted. In the past, model based insertion has also been used where the vertebra needs to be segmented and matched to a model of a standard vertebra of that type. However, this model-based planning requires a segmentation step, which can be a relatively lengthy action and may not be suitable accurate or succeed if the image is of bad quality.

Despite the above, there remains a need for automated planning methods and systems which can reliably provide planning information for proper pedicle screw placement in the spine of individual patients.

SUMMARY OF EMBODIMENTS OF THE PRESENT INVENTION

Embodiments of the invention provide automated guidance for inserting pedicle screws (typically directly) into 3D reconstructions of images such as, for example, CT images.

In some embodiments, apart from the 3D reconstruction of the CT data, no preprocessing is required (i.e., no registration is required) which can facilitate a rapid planning protocol/output.

In some embodiments, a user electronically selects regions (i.e., points) on a posterior of a target vertebra, approximately where he/she would like to insert pedicle screws and the system can automatically calculate an optimal placement and generate graphic representations of in-place screws, as well as provide sizing information about the appropriate length and diameter screws.

Embodiments of the invention are directed to an automated or semi-automated method of planning for placement of pedicle screws. The method includes: providing a three dimensional (3D) image of a target vertebra of a patient; electronically defining a first coordinate axis system using a first axis extending in an anatomical right to left direction across a target vertebra; electronically ray casting the 3D image of the target vertebra in an anterior direction that is anterior to the first axis; electronically identifying a vertebral foramen (VF) based at least in part on the ray casting; electronically calculating a second coordinate axis system aligned with an orientation of the VF; and electronically identifying placement and sizing of at least one pedicle screw using the second coordinate axis system.

The first and second coordinate systems can be Cartesian coordinate systems.

The first axis can be a first x-axis, a z-axis can extend in a superior/inferior direction and a y-axis can extend in an anterior/posterior direction.

The ray casting can identify points on a boundary of bone tissue.

The method can include displaying the provided 3D image of the target vertebra. The first x-axis can be generated based on user input of first and second points, spaced apart in the right to left direction, on a posterior of the displayed target vertebra.

The identifying the VF can be carried out by: i) determining a midpoint between the first and second points from the user input, ii) for points along a line extending in the anterior direction from the midpoint, the electronically ray casting comprises applying a first ray casting that is carried out in the left and right directions to determine an intersection surface associated with bone tissue, iii) from the intersection surface, determining a point or points in an interior of the VF, and iv) from the interior point or points of the VF, applying a second ray casting to determine intersection points with the bone tissue that represent an inner surface of the VF.

The second ray casting may include spherically distributed ray casting to identify a point cloud having a cylindrical shape.

The method can further include electronically using the cylindrical shape to identify an orientation of the VF and a middle point of the VF.

The second ray casting can include casting rays in the left and right directions from regularly spaced apart points above and below the middle point of the VF, registering points until rays do not hit bone tissue within a distance of +1-50% of a radius of the cylindrical shape fitted to the VF, and adjusting the middle point of the VF along the z-axis to be an average of the z-axis position of the registered points.

Identifying the orientation of the VF can be performed by electronically fitting a cylindrical model to the VF by approximating plane normals for each point neighborhood in the point cloud derived from the spherically distributed ray casting, fitting a plane to the collection of normal vectors which represents a cross-section of the cylinder, and using the normal of the cross-section plane to define a cylinder centerline direction of the cylinder.

The method can include electronically tilting the z-axis of the second coordinate axis system about 10 degrees in the anterior direction relative to an orientation in the first coordinate system then calculating an anatomical based orientation of the y-axis and x-axis of the second coordinate system based on the tilted z-axis.

The method can include electronically ray casting relative to a middle point of the VF in the second coordinate axis system to identify boundary points of cortical bone, then determining a perimeter of a vertebral body from the boundary points, calculating a middle body location of the vertebral body (bodyMid) spaced apart from and adjacent the VF, and updating the second coordinate axis system based on the defined middle body location to thereby adjust for rotation of the vertebra about the z-axis.

The pedicle screw placement and sizing can include determining a first control point left or right of a midpoint of the VF in the second coordinate axis system, the control point being adjacent to the VF and within bone tissue but sufficiently distant to the VF to prevent a properly placed and sized pedicle screw from penetrating the VF.

The pedicle screw placement and sizing can include determining a second control point anterior to the vertebra, along the y-axis from the midpoint of the VF in the second coordinate axis system. The pedicle screw placement can be defined by a line through the first and second control points.

The method can include allowing a manual adjustment of the electronically identified pedicle screw placement. The first control point can be set to be a fixed center of rotation for a user for the manual adjustment of the pedicle screw placement.

The method can further include: electronically ray casting the target vertebra from a point in the middle of the VF (holeMid) to identify a perimeter of a vertebral body; electronically calculating a middle body location of the vertebral body (bodyMid); electronically ray casting the target vertebra laterally in a right to left direction in increments in up and down directions relative to holeMid to identify pedicle heights; electronically defining a front/anterior position where the pedicle screws will point using the equation: bodyMid+(bodyMid−holeMid)×1.5; electronically defining right and left lines of a trajectory of respective right and left pedicle screws from a pedicle to a front position; generating a graphical representation of physical pedicle screws with the graphical representation placing the pedicle screws perpendicular to the cylinder shape in an anterior direction from the pedicles; and electronically providing size and length parameters of right and left physical pedicle screws as the electronically identifying the placement and sizing.

The method can include determining the intersection points of vertebra boundary along a pedicle screw trajectory at the front and back of the vertebra, and determining the size of the pedicle screw as a predefined proportion of the distance between the intersection points.

The electronically identifying placement and sizing of one or two pedicle screws for a single vertebra can be carried out in between 100 and 200 milliseconds.

Other embodiments are directed to clinician workstations. The workstations include: at least one display and a circuit in communication with the at least one display. The circuit includes and/or is in communication with at least one processor configured to: provide a three dimensional (3D) image of a target vertebra of a patient; define a first coordinate axis system using a first axis extending in an anatomical right to left direction across a target vertebra; ray cast the 3D image of the target vertebra in an anterior direction that is anterior to the first axis; identify a vertebral foramen (VF) based at least in part on the ray casting; calculate a second coordinate axis system aligned with an orientation of the VF; and identify placement and sizing of at least one pedicle screw using the second coordinate axis system.

The circuit with the at least one processor can direct the display to display the provided 3D image of the target vertebra and accept user input of first and second points spaced apart in the right to left direction, on a posterior of the displayed target vertebra. The first x-axis can be generated based on the user input.

The VF can be identified by: i) determining a midpoint between the first and second points from the user input, ii) for points along a line extending in the anterior direction from the midpoint, the electronically ray casting comprises applying a first ray casting that is carried out in the left and right directions to determine an intersection surface associated with bone tissue, iii) from the intersection surface, determining a point or points in an interior of the VF, and iv) from the interior point or points of the VF, applying a second ray casting to determine intersection points with the bone tissue that represent an inner surface of the VF.

The identification of the pedicle screw placement and sizing can include determining a first control point left or right of a midpoint of the VF in the second coordinate axis system, the control point being adjacent to the VF and within bone tissue but sufficiently distant to the VF to prevent a properly placed and sized pedicle screw from penetrating the VF.

The identification of the pedicle screw placement and sizing can include determining a second control point anterior to the vertebra, along the y-axis from the midpoint of the VF in the second coordinate axis system. The pedicle screw placement can be defined by a line through the first and second control points.

Still other embodiments are directed to a system for evaluating 3-D spinal patient image data for pedicle placement planning. The system includes a pedicle placement planning module that includes at least one processor and at least one display in communication with the pedicle planning module comprising the at least one processor. The pedicle placement module can be configured to carry out the methods of any of Claims 1-16.

It is noted that any one or more aspects or features described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION OF EMBODIMENTS OF THE INVENTION

Figure 1A:
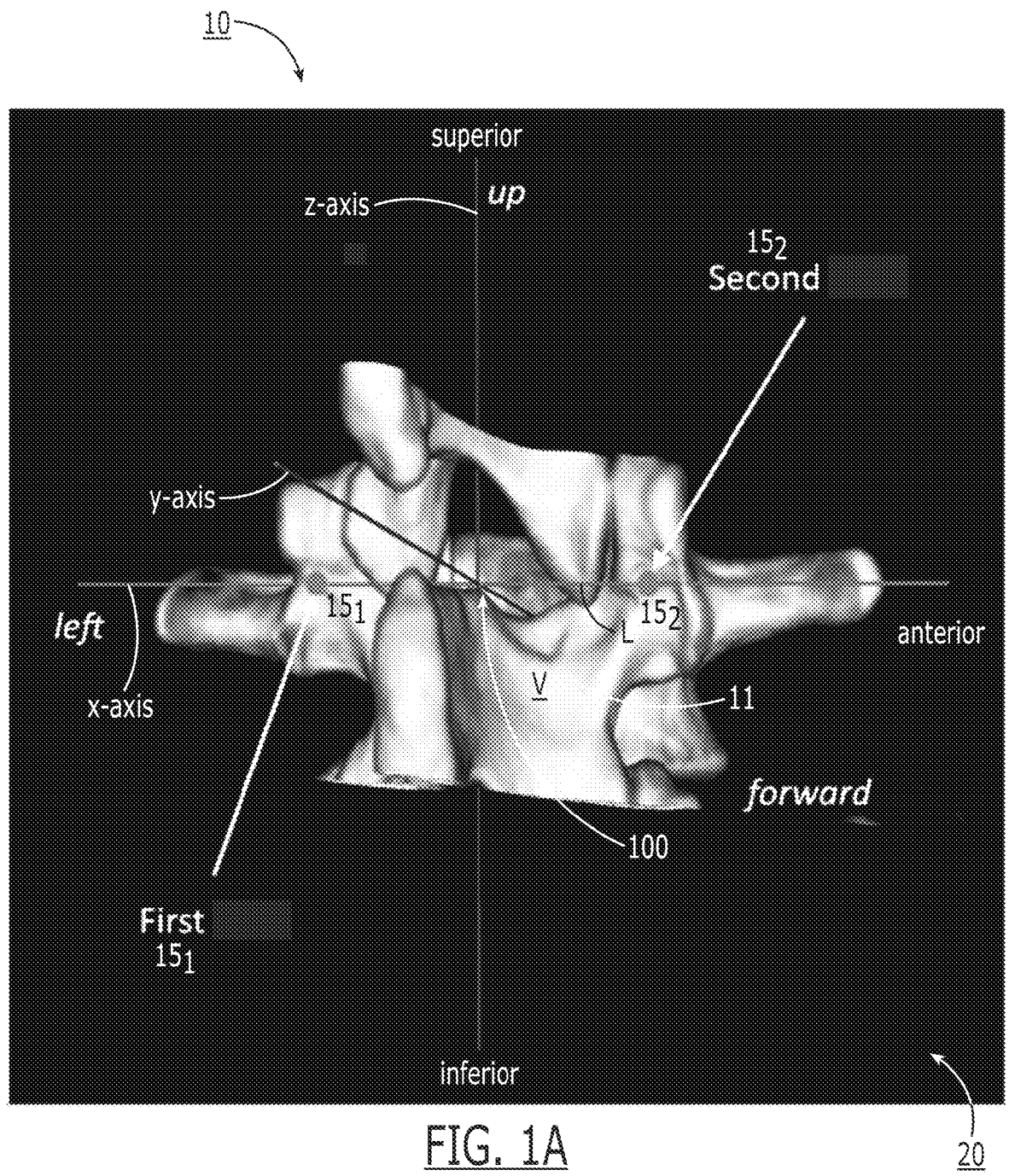
FIG. 1A is a schematic illustration of a planning system comprising a display with a three-dimensional image of a portion of a spine (anterior or forward view) on a display allowing user input for identifying a target vertebra for pedicle screw(s) according to embodiments of the present invention.

The present invention will now be described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout. It will be appreciated that although discussed with respect to a certain embodiment, features or operation of one embodiment can apply to others.

In the drawings, the thickness of lines, layers, features, components and/or regions may be exaggerated for clarity and broken lines (such as those shown in circuit or flow diagrams) illustrate optional features or operations, unless specified otherwise.

The term "Fig." (whether in all capital letters or not) is used interchangeably with the word "Figure" as an abbreviation thereof in the specification and drawings. In addition, the sequence of operations (or steps) is not limited to the order presented in the claims unless specifically indicated otherwise.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items. Like numbers refer to like elements throughout. In the figures, the thickness of certain lines, layers, components, elements or features may be exaggerated for clarity.

As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

The term "about" means that the recited parameter may vary somewhat from the recited value, typically within +/−20% or +/−10%.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when a feature, such as a layer, region or substrate, is referred to as being "on" another feature or element, it can be directly on the other element or intervening elements may also be present. In contrast, when an element is referred to as being "directly on" another feature or element, there are no intervening elements present. It will also be understood that, when a feature or element is referred to as being "connected" or "coupled" to another feature or element, it can be directly connected to the other element or intervening elements may be present. In contrast, when a feature or element is referred to as being "directly connected" or "directly coupled" to another element, there are no intervening elements present. Although described or shown with respect to one embodiment, the features so described or shown can apply to other embodiments.

The term "circuit" refers to an entirely software embodiment or an embodiment combining software and hardware aspects, features and/or components (including, for example, at least one processor and software associated therewith embedded therein and/or executable by and/or one or more Application Specific Integrated Circuits (ASICs), for programmatically directing and/or performing certain described actions or method steps). The circuit can reside in one location or multiple locations, it may be integrated into one component or may be distributed, e.g., it may reside entirely in a workstation or single computer, partially in one workstation, cabinet, or computer, or totally in a remote location away from a local display at a workstation.

The term "visualization" means to present images to a user or users for viewing. The visualization can be in a flat 2-D image and/or in 2-D that appears to be 3-D images on a display, data representing features (physical, electrical or magnetic and the like) with different visual characteristics such as with differing intensity, opacity, color, texture and the like. The actual visualization can be shown on a screen or display so that the volume or region (e.g., anatomical vertebra structure) is in a flat 2-D and/or in 2-D that appears to be 3-D volumetric images, optionally with data representing features or electrical output with different visual characteristics associated with bone having adjustable visualization intensity, opacity, color, texture and the like.

The term "GPU" refers to a Graphic Processing Unit which is typically at least one processor that can be used with a CPU.

Embodiments may be particularly suitable for use with medical image data sets from any imaging modality including MRI and CT. The images may optionally be generated using Direct Volume Rendering (DVR). DVR, a term well-known to those of skill in the art, comprises electronically rendering a medical image directly from data sets to thereby display visualizations of target regions of the body, which can include color as well as internal structures, using three-dimensional (3D) or time-resolved 3D data. In contrast to conventional iso-surface graphic constructs, DVR does not require the use of intermediate graphic constructs (such as polygons or triangles) to represent objects, surfaces and/or boundaries. However, DVR can use mathematical models to classify certain structures and can use graphic constructs.

The term "automatically" means that the operation can be substantially, and typically entirely, carried out without human or manual input, and is typically programmatically directed or carried out. The automated planning procedure can be initiated by user input via a GUI to select or identify a target vertebra for the pedicle screw(s). The term "electronically" includes both wireless and hard-wired connections between components.

The term "without preprocessing" means that the processing required to perform the pedicle screw placement is initiated when the user initiates the procedure, with subsecond processing times. Thus, the intended usage is experienced "on-the-fly" and no precursing steps of, for instance, image processing and analysis such as segmentation or registration, are needed.

A data set for the visualizations can be defined as a number of grid points in G dimensions, where there are a V number of values in each grid point. The term "multi-dimensional" refers to both components, grid G and variates V, of the data sets. For data sets having a $V \geq 1$, the data set is referred to as multi-variate. As examples, a normal medical data set has $G=3$ and $V=1$, and a normal time-dependent volume has $G=4$ and $V=1$, a volume describing flow will have $G=3$ and $V=3$ (three values, since the velocity is a 3D vector). The data sets of the instant invention for medical images will typically have G and V values of $G \leq 4$ and $V \leq 6$. As known to those of skill in the art, traditional medical systems are bound by the 2D slice format used by the imaging modalities and use this base to construct higher-dimensional data.

The term "bone tissue" refers to osseus tissue in the human anatomy, as opposed to softer tissue such as muscle, ligaments, nerves, vessels, etc as well as liquids, including blood, and cavities. In an image data set from a Computed Tomography scanner, the value range of bone is typically about 200-3000 Hounsfield units. The two main types of bone tissue are cortical bone and cancellous bone, and "bone tissue" can, in different embodiments, of the invention refer to both or either type.

Any document (article, web publication, patent, and patent application) identified or referenced in this document (including the background or specification) is hereby incorporated by reference as if recited in full herein.

The term "ray casting" is well known to those of skill in the art and refers to electronically casting rays to sample volumetric data sets to solve a variety of problems in computer graphics and computational geometry. In this document, the term "spherical ray casting" refers to ray casting from a center point in all directions to identify a volume that corresponds to a shape, orientation and location of a vertebral foramen. The term "point cloud" refers to a volumetric space in a 3D image associated with end point portions of rays used to identify a volumetric space and/or bone or tissue bounding a volumetric space, i.e., a VF of a target vertebra. See, by way of example only, Dodin, P., Martel-Pelletier, J., Pelletier, J.-P., Abram, F. (2011) A fully automated human knee 3D MRI bone segmentation using the ray casting technique. Medical & Biological Engineering & Computing, December 2011, Volume 49, Issue 12, pp 1413-1424; and Kronman A., Joskowicz L., Sosna J. (2012) Anatomical Structures Segmentation by Spherical 3D Ray Casting and Gradient Domain Editing. In: Ayache N., Delingette H., Golland P., Mori K. (eds) Medical Image Computing and Computer-Assisted Intervention—MICCAI 2012. MICCAI 2012. Lecture Notes in Computer Science, vol 7511. Springer, Berlin, Heidelberg. The contents of these documents are hereby incorporated by reference as if recited in full herein.

Figure 8A:
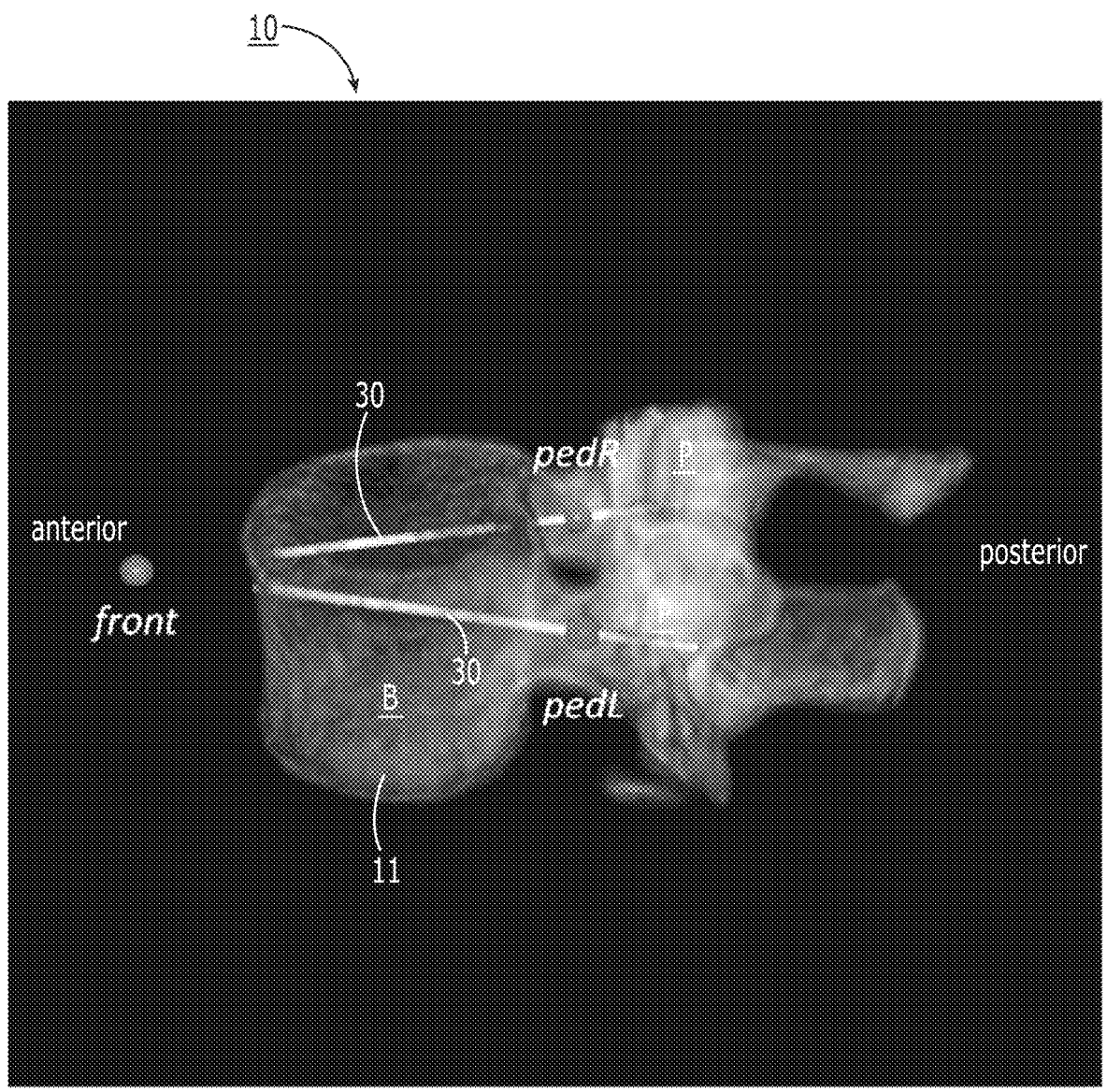
FIG. 8A illustrates the planning system electronically identifying placement trajectories for pedicle screws through the respective pedicles and into the vertebral body (shown in an anterior posterior view) according to embodiments of the present invention.
Figure 8B:
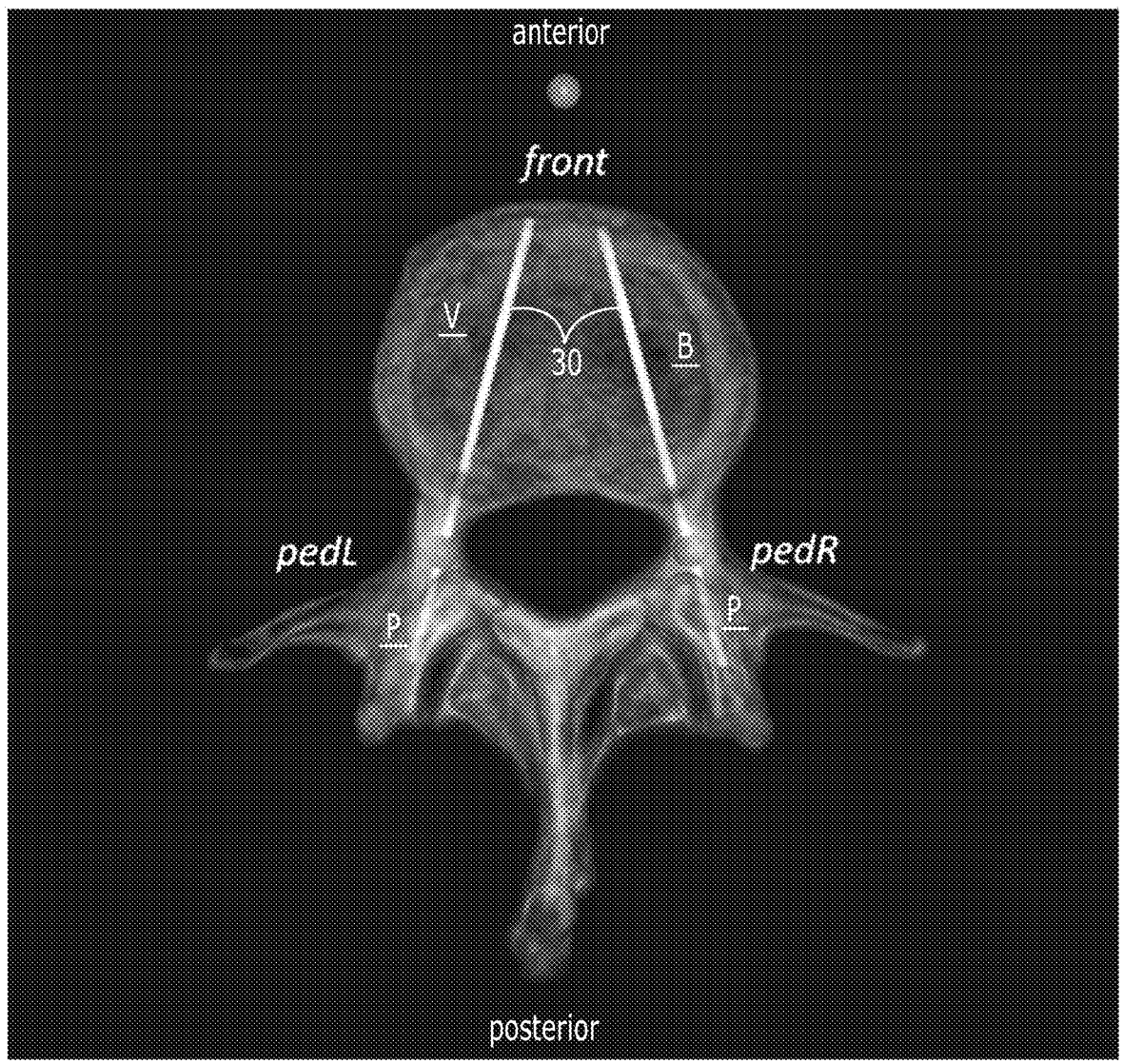
FIG. 8B illustrates the planning system electronically identifying placement trajectories for pedicle screws through the respective pedicles and into the vertebral body (shown in a superior view) according to embodiments of the present invention.

Embodiments of the invention are particularly suitable for identifying appropriate (typically optimal) placement one or more pedicle screws 30 at one or more level in a vertebra V of the spine (FIGS. 8A, 8B). In particular embodiments, one or more pedicle screws can be placed at one or more vertebra from T1-L5 although it is contemplated that only certain spine regions may be targeted for actual placement, e.g., any one or more levels between T1-T12 or L1-L5, or between T11-L4, for example.

The term "rapid" means for a respective patient, the planning information for pedicle screw placement for a respective single vertebrae of a patient using a 3-D patient image data set can be carried out automatically, typically initiated based on user input to select a first or only vertebra location, in a range of 10 seconds to 10 milliseconds, typically in about 100-300 milliseconds per vertebra, more typically in about 200 ms per vertebra. The automated generated planning information can include computed measurements of location, orientation, angular insertion trajectory (and a visual display of same), and calculated lengths and diameters of one or more pedicle screws 30 that matches a patient's needs/anatomy. Different size pedicle screws 30 can be identified for a single level/single vertebra.

Referring to FIGS. 1A, 1B, 8A and 8B, the automated pedicle screw placement planning systems 10 can provide planning assistance and/or surgical guidance for insertion placement, orientation and/or trajectory of pedicle screws 30 through respective pedicles P and into a target vertebral body B of a vertebra V. The screws 30 can be selected with a length sufficient to extend through 80% to 95% of the vertebral body B. The 3D image 11 shown on a display 20 according to embodiments of the invention employ three dimensional (3D) reconstruction of patient image data sets such as a 3D computed tomography (CT) data set, an MRI data set or a data set that combines both CT and MRI image data (e.g., a composite image data set). Thus, while the below description is primarily discussed for (low dose) CT data using patient data sets that can be obtained from a PACS (picture archiving and communication) system, the invention is not limited thereto.

Figure 2A:
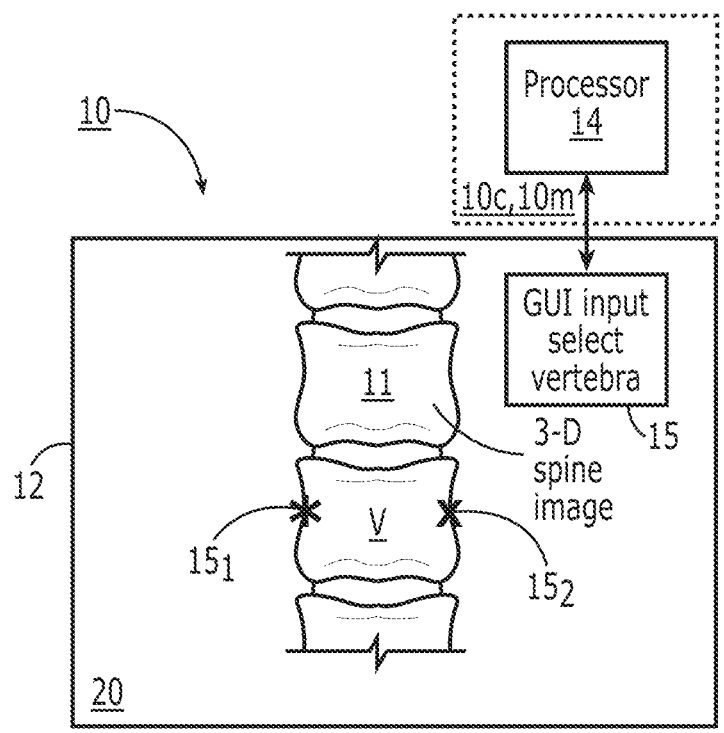
FIGS. 2A and 2B are schematic illustrations of example clinician workstations comprising or coupled to the planning system according to embodiments of the present invention.
Figure 2B:
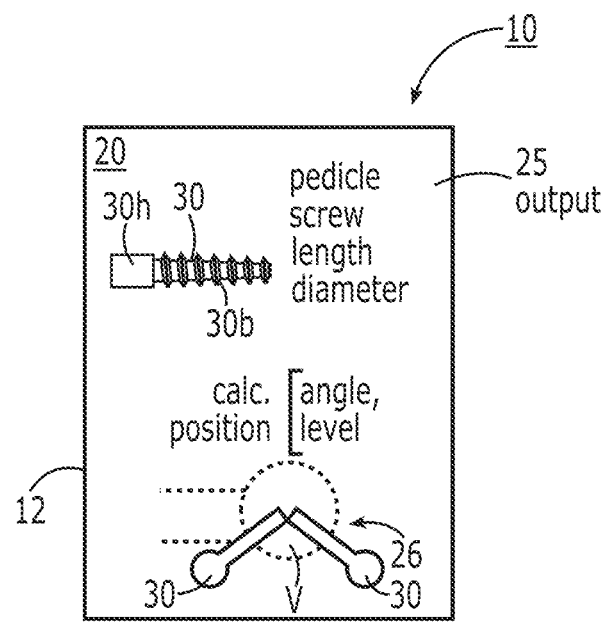

Referring to FIGS. 2A and 2B, the systems 10 can include or be coupled to (in communication with) a display 20 which can display a 3D (reconstructed) image 11 of a patient's spine (typically a human patient but embodiments of the invention may also be suitable for animal patients). The systems 10 can be part of a clinician workstation 12. The systems 10 can include a circuit 10c with at least one processor 14 and a UI control 15 that allows a user to select a target vertebra V. GUI (Graphic User Input) controls and other User Input (UI) controls, including UI controls that allow click and/or touch input and touch gestures using a touch screen, are widely used and well known to those of skill in the art and will not be explained in further detail herein. GUI controls and/or other UI controls 15 can be in communication with a display 20 such as that associated with a clinician workstation 12 to allow selection of one or more target vertebra for pedicle screw placement.

As shown in FIG. 2B, the automated generated planning information output 25 can include a graphical representation 26 of the proper placement of the pedicle screws 30 based on computed measurements to place the screws medially through pedicles into a vertebral body B anterior to the VF and calculated sizes 25 of lengths and diameters of one or more pedicle screws 30 that matches a patient's needs/anatomy. Different size pedicle screws 30 can be identified for a single level/single vertebra. As shown in FIG. 9B, the right side pedicle screw 30 can have a different length (46 mm versus 47 mm for the left pedicle screw). As shown, each screw 30 can have the same diameter (5.5 mm). The planning system 10 can display an output comprising sizing information 25 such as a head $30h$ size and/or a body size $30b$ of a respective pedicle screw 30.

The system 10 can be configured to define a first "global" coordinate system 100, typically a Cartesian coordinate system with x, y and z axes that will subsequently be replaced with a second "local" anatomically-based coordinate system 200 (FIG. 5) with the z-axis moved to be more anterior to extend through the vertebral foramen (VF) as will be discussed below. The x-axis corresponds to a right-left direction (coronal plane direction). The z-axis corresponds to the superior-inferior direction (up/down or head/feet direction), perpendicular to the x-axis and y-axis. The y-axis corresponds to the anterior/posterior direction (forward/back direction or sagittal plane direction), perpendicular to the x-axis and z-axis. Other three-dimensional coordinate systems such as cylindrical coordinate systems (an extension of polar coordinates to three dimensions) or spherical coordinate systems may alternatively be used.

Figure 1B:
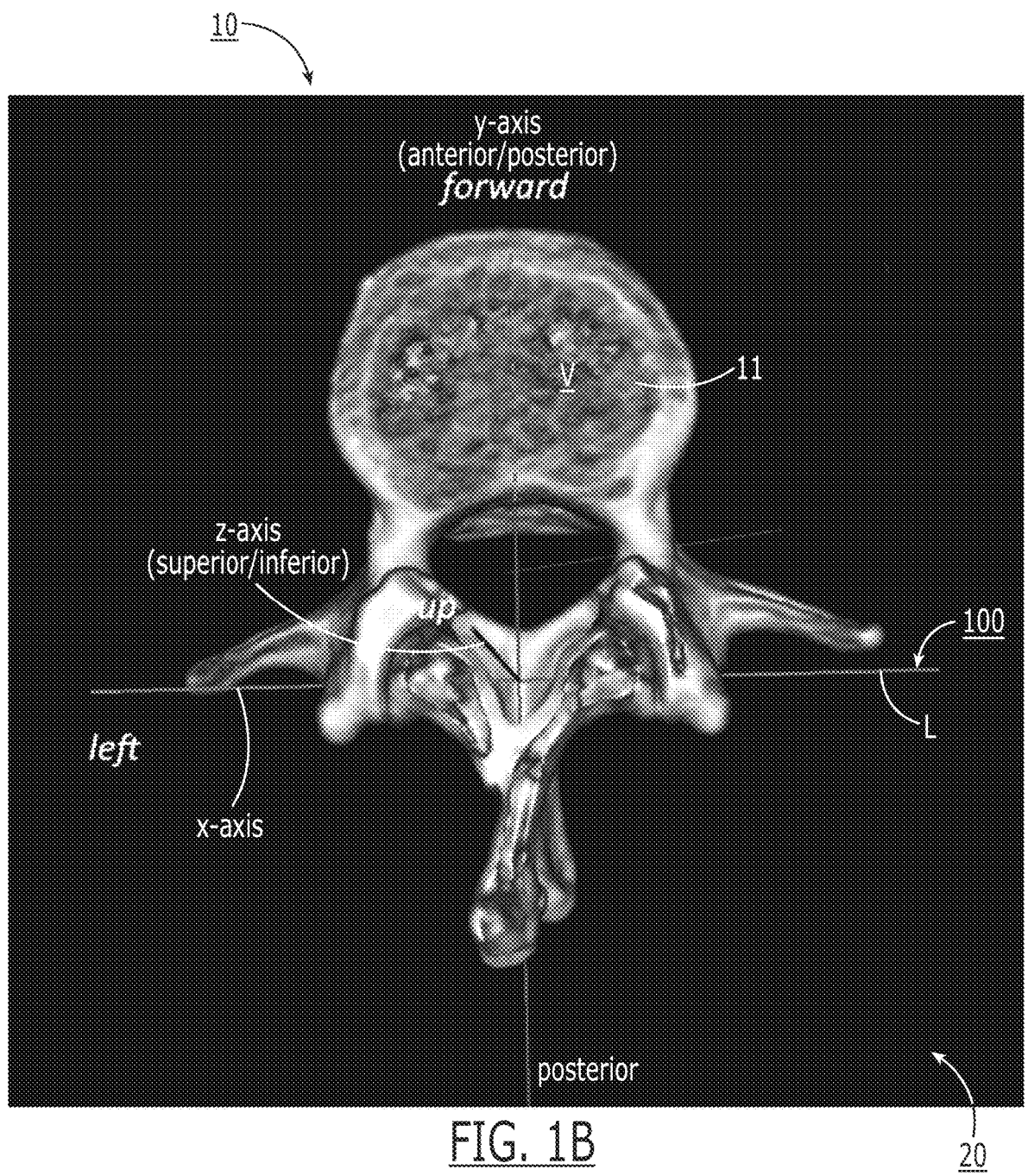
FIG. 1B is a superior view of the spine shown in FIG. 1A illustrating an initial coordinate system axis used by the planning system according to embodiments of the present invention.

In some embodiments, the system 10 can be configured to allow a user to select a plurality, shown as two, spaced apart points or regions on a posterior or back of the target vertebra V at a location approximate to where screws 30 are expected to penetrate the vertebra, shown as $15_1$, $15_2$ on the image 11 shown on the display 20 (see, e.g., FIGS. 1A and 1B). A line L can be drawn through these selected regions $15_1$, $15_2$ to define an axis of the first coordinate system 100, which can be set as a first x-axis. The user selection of the two points or regions $15_1$, $15_2$ can initiate the automated planning actions of the planning system 10.

Embodiments of the present invention provide an automatic (or semi-automatic) planning system 10 for inserting pedicle screws using 3D reconstructions of CT images. Apart from the 3D reconstruction of the CT image data, no pre-processing of the image data, such as segmentation, is required to identify the first coordinate system 100.

To start the rapid output of the automated planning system 10, a user can electronically select, via a UI or GUI control 15 (i.e., a touch, gesture or click), a target vertebra V on the display 20, at a location that is approximately where he/she would like to insert pedicle screws and the automated planning system 10 electronically calculates a placement and insertion trajectory for a pedicle screw(s), as well as providing patient-based sizing information (length and diameter) regarding pedicle screws for the surgical procedure. In other embodiments, the system 10 can automatically identify the first coordinate system and/or x-axis thereof by automatically selecting target locations for pedicle screw penetration at a posterior surface of the target vertebra without requiring user input for this selection.

The following describes exemplary actions that can be carried out by the automated planning system 10. For ease of discussion, variables used for the automated planning system 10 below are named below with italic text.

As noted above, a user of the system 10 can electronically select and/or place two initial points $15_1$, $15_2$ on the back (posterior) of the target vertebra V (FIG. 1A). The points $15_1$, $15_2$ can be spaced apart in a right-left direction and placed approximately where the screws are expected to penetrate the vertebra, but the locations do not have to be exact, since the insertion location(s) will likely be overridden by the automated planning system output.

As shown in FIG. 1B, the two points $15_1$, $15_2$ can be used to generate a line, left, which can be used as the initial x-axis for the vertebra V of the first coordinate system 100. The user might click the points in any order and the line L of the x-axis can be flipped if it points towards negative x (positive x is left). The middle point on this line (the average of the two points) defines a point avg which can be used to set a location of the other axes of the first coordinate system 100.

Figure 3:
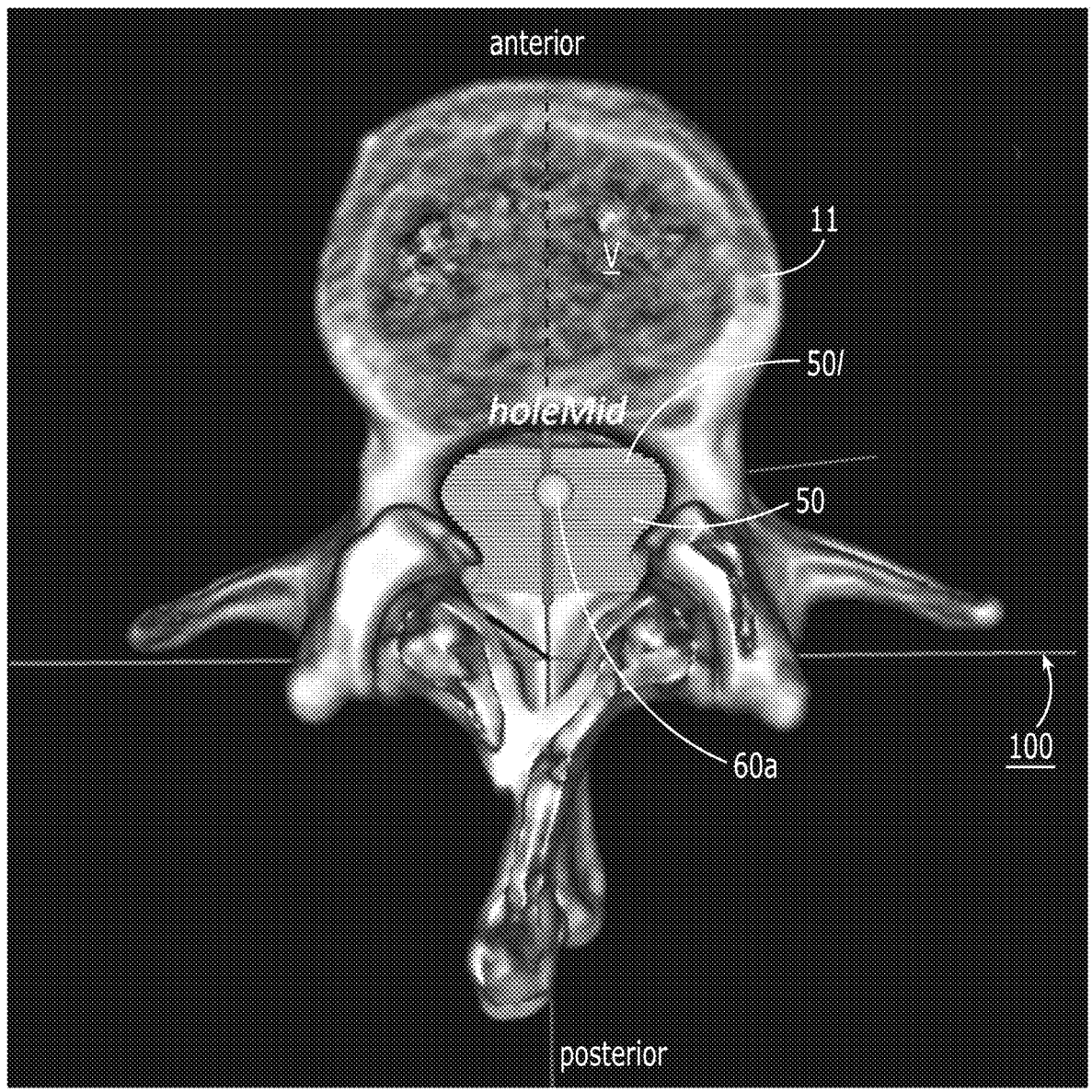
FIG. 3 illustrates the planning system with the target vertebra shown in FIG. 1A electronically identifying the associated vertebral foramen ("VF") according to embodiments of the present invention.

Referring to FIG. 3 and FIG. 4, a plurality of points are electronically generated and/or placed with ray casting in a 3D volume of the patient image 11, from any desired (camera) angle of the image data volume in 3D. A ray can be programmed to stop when it encounters or hits dense tissue (such as bone). A visible density of the bone in the 3D image of the patient can be adjusted by the user using the UI control 15.

Still referring to FIG. 3 and FIG. 4, the planning system 10 can electronically locate an approximate center $60a$ for the vertebral foramen (VF). The VF is the hole where the spinal cord goes through the vertebra. The approximate forward (anterior) direction can be calculated by taking the cross product between left and the first (i.e., "global") z-axis, which can be electronically stored and defined as a variable up. This calculation will result in a variable termed "forward".

The system 10 can electronically evaluate the 3D image by moving along a line that is parallel to or corresponds to the y-axis, typically starting at avg in or along the forward line. At every defined increment, typically between 0.1 and 1 mm, such as about 0.5 mm, the system 10 can ray cast left and right (left and -left) with rays 50, until bone is found. If both the left and the right rays 50 hit bone, a line 50l between the hit points can be generated and electronically stored/saved. This process can be repeated until a defined number of lines such as between 10-1000 lines, (i.e., at least 10 lines) are (successively) found that are shorter than 5 mm. This indicates that the movement in the forward direction has resulted in a position inside the vertebral body B and the whole VF has been identified/scanned.

To reduce impact of outliers, the series of lengths of the hit lines 50l can be smoothed. The length of a hit line can be redefined as the weighted sum of the lengths of the hit line and a plurality (i.e., 4) of its closest neighboring hit lines. For example, the smoothing operation can be performed as an averaging convolution applying the filter kernel $\frac{1}{5}*[1\ 1\ 1\ 1\ 1]^T$ to the hit line length series.

The longest of the (optionally smoothed) lines 50l can be identified and its middle point can be calculated and stored as holeMid 60. This holeMid 60 region or point (FIG. 4A) represents the approximate middle point of the VF sideways (in a direction parallel to or along the y-axis).

Next, the planning system 10 can find the orientation of the bone that defines the VF. This orientation can be a major descriptor for a local (second) coordinate system of the target vertebra.

Figure 4A:
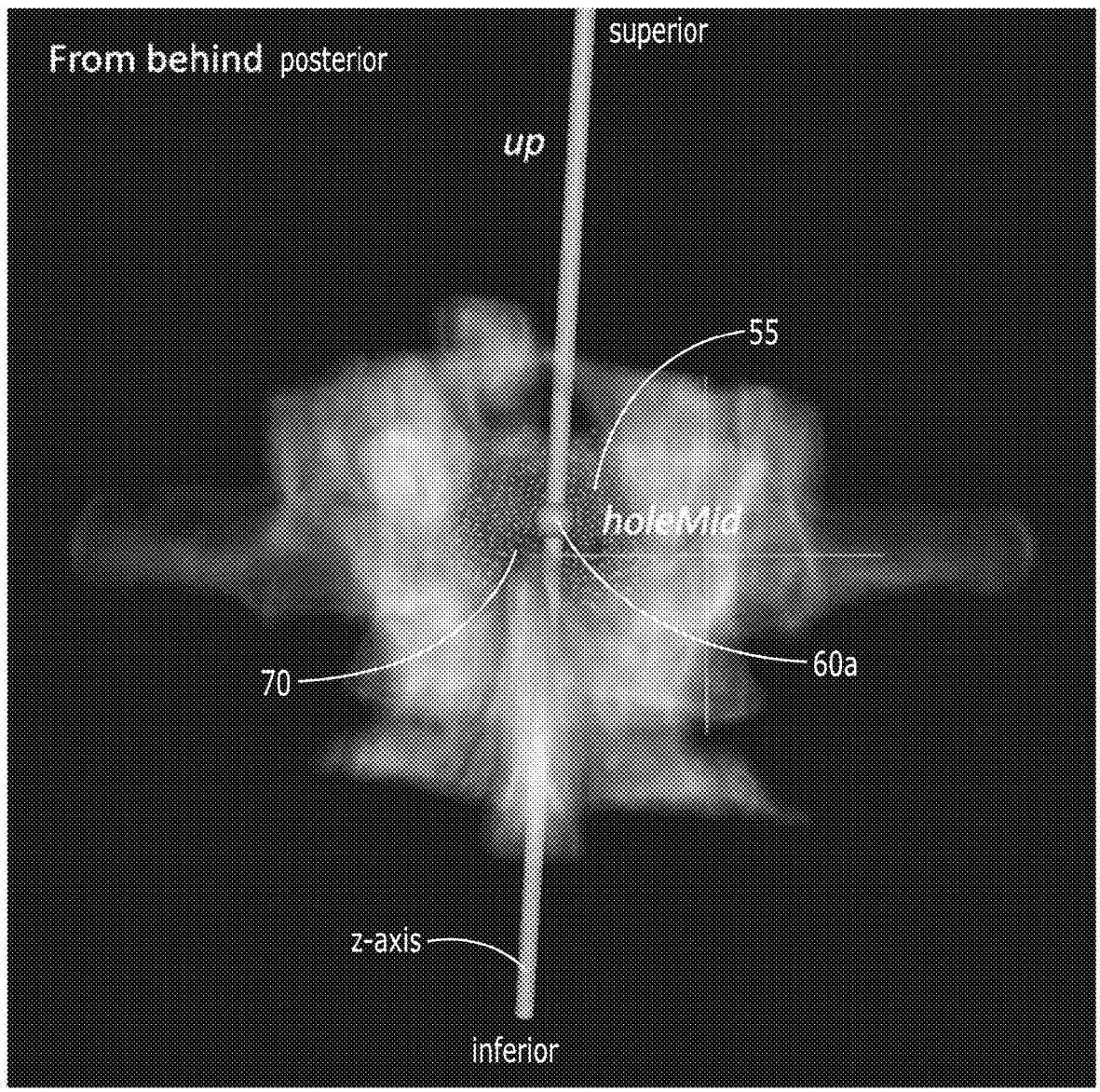
FIG. 4A, FIG. 4B and FIG. 4C illustrate the planning system with the target vertebra shown in FIG. 1A electronically ray casting to identify a volume associated with the VF and an associated center thereof (holeMid) according to embodiments of the present invention.
Figure 4B:
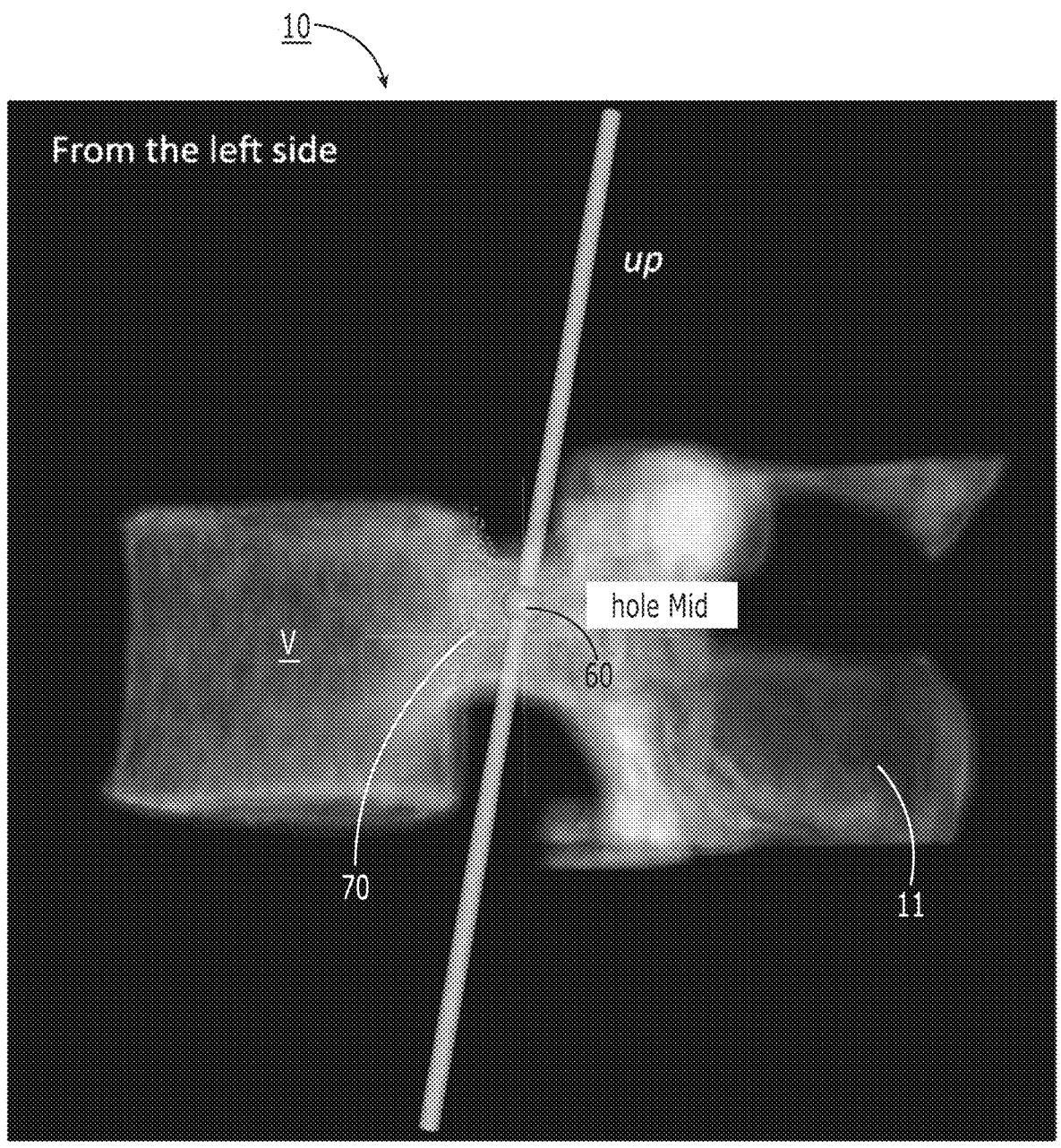
Figure 4C:
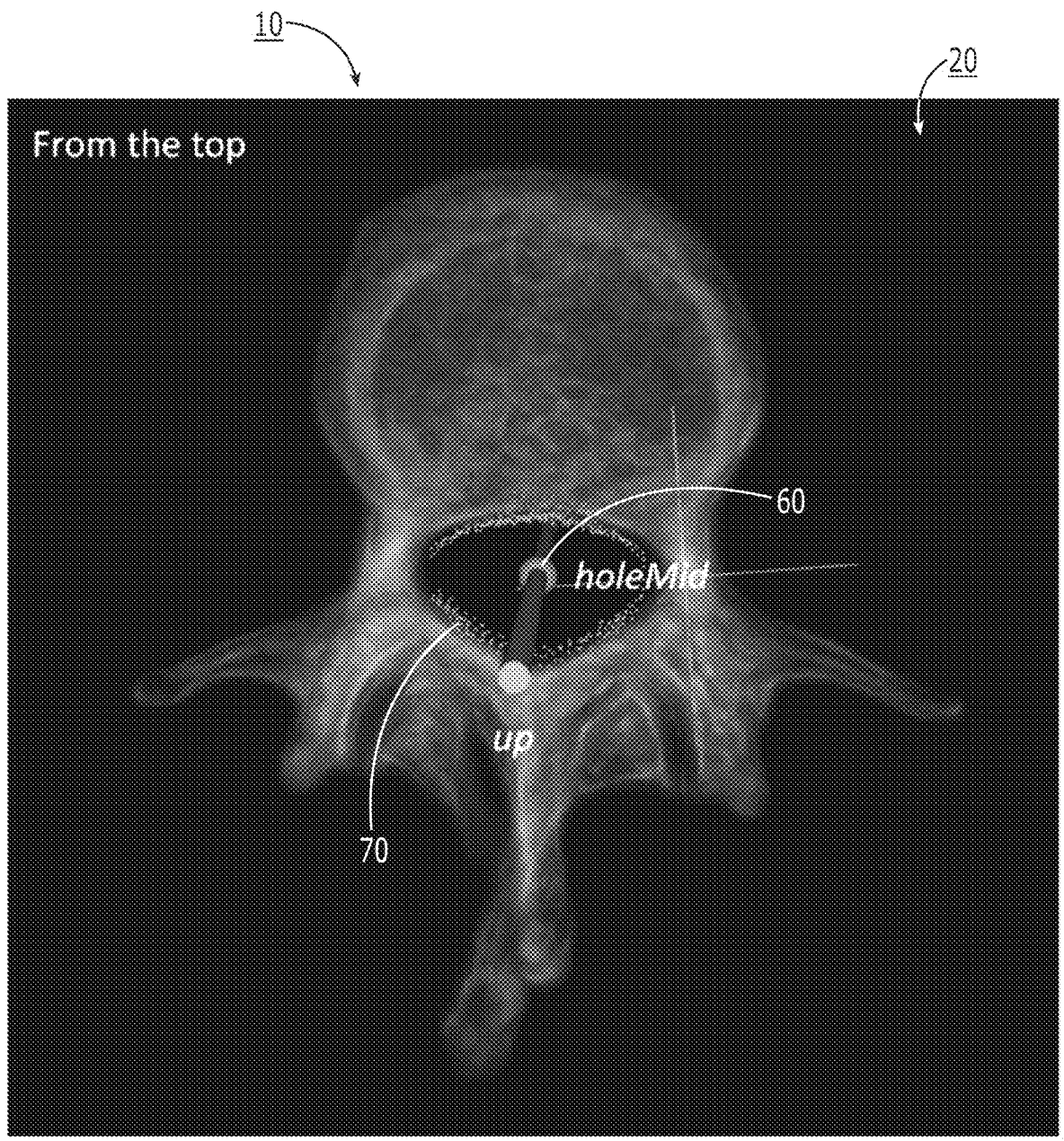

Referring to FIGS. 4A-4C, from holeMid 60, a spherical ray casting in all directions can be performed. The number of rays 55 can be dynamically adjusted to balance accuracy and performance. The rays 55 can be created by approximately uniformly distributing a number of points on a sphere or non-uniformly distributing the points or in other manners. Different approaches for approximately uniform distribution of points on a sphere are discussed in Saff, E. B., Kuijlaars, A. B. J. (1997) Distributing many points on a sphere, The Mathematical Intelligencer, the contents of which are hereby incorporated by reference as if recited in full herein.

The system 10 can obtain the ray directions for each distributed point p and create the vector d=p−holeMid. For each direction, a ray 55 can be generated that starts in holeMid 60 and has the direction d. The intersection points where rays hit bone can be identified. The average distance from the bone intersection points to holeMid 60 can be calculated. Bone intersection points that are farther away from holeMid 60 than the average distance can be removed or not included for further processing. The (optionally reduced) set of bone intersection points constitutes a point cloud 70 that can be used to define the inner edges of the VF. The point cloud 70 can resemble the shape of a cylinder, which approximates the part of the spinal cord that goes through the vertebra. The system 10 can identify a best matching cylinder for the points in the point cloud 70. This will give a new middle point for the VF, redefining the holeMid 60 position, and its orientation.

The matching of the cylinder shape to the point cloud can be performed by standard methods well known in the field, see, for example, Lukacs, G., Martin, R. R. Marshall, A. D. (1998) Faithful least-squares fitting of spheres, cylinders, cones and tori for reliable segmentation. Lecture Notes in Computer Science 1406, pp. 671-686, the contents of which are hereby incorporated by reference as if recited in full herein. The matching can also be done by approximating plane normals for each point neighborhood in the point cloud, fitting a plane to the collection of normal vectors which represents a cross-section of the cylinder, and using the normal of the cross-section plane to define the cylinder centerline direction, as follows: For substantially all points (typically every point) in the point cloud 70 (FIGS. 4A-4C), the system 10 can electronically gather all the nearest neighbors. The term "substantially all" for these points refers to at least 80% of the points in the point cloud. For the gathered neighbors, the system 10 can electronically derive the best fitting plane for the points using linear regression minimizing the sum of distances from the points to the plane. The distance threshold for an adjacent point to be included in the neighborhood can be adjusted, typically between 1-8 mm, but testing has shown that a radius of about 5 mm works well for adult patients. If a point has no more than two neighbors, it can be treated as an outlier and can be omitted or skipped. A new, auxiliary, point cloud can then be created from the derived set of normal vectors. The system 10 can again use linear regression to fit a plane to the auxiliary point cloud, a plane representing the cross-section of the cylinder. The system 10 can then derive the normal of the cross-section plane to define the VF centerline direction. Furthermore, the center of the original point cloud, derived by averaging the point cloud positions, can be used to define the position of the VF centerline.

Figure 4D:
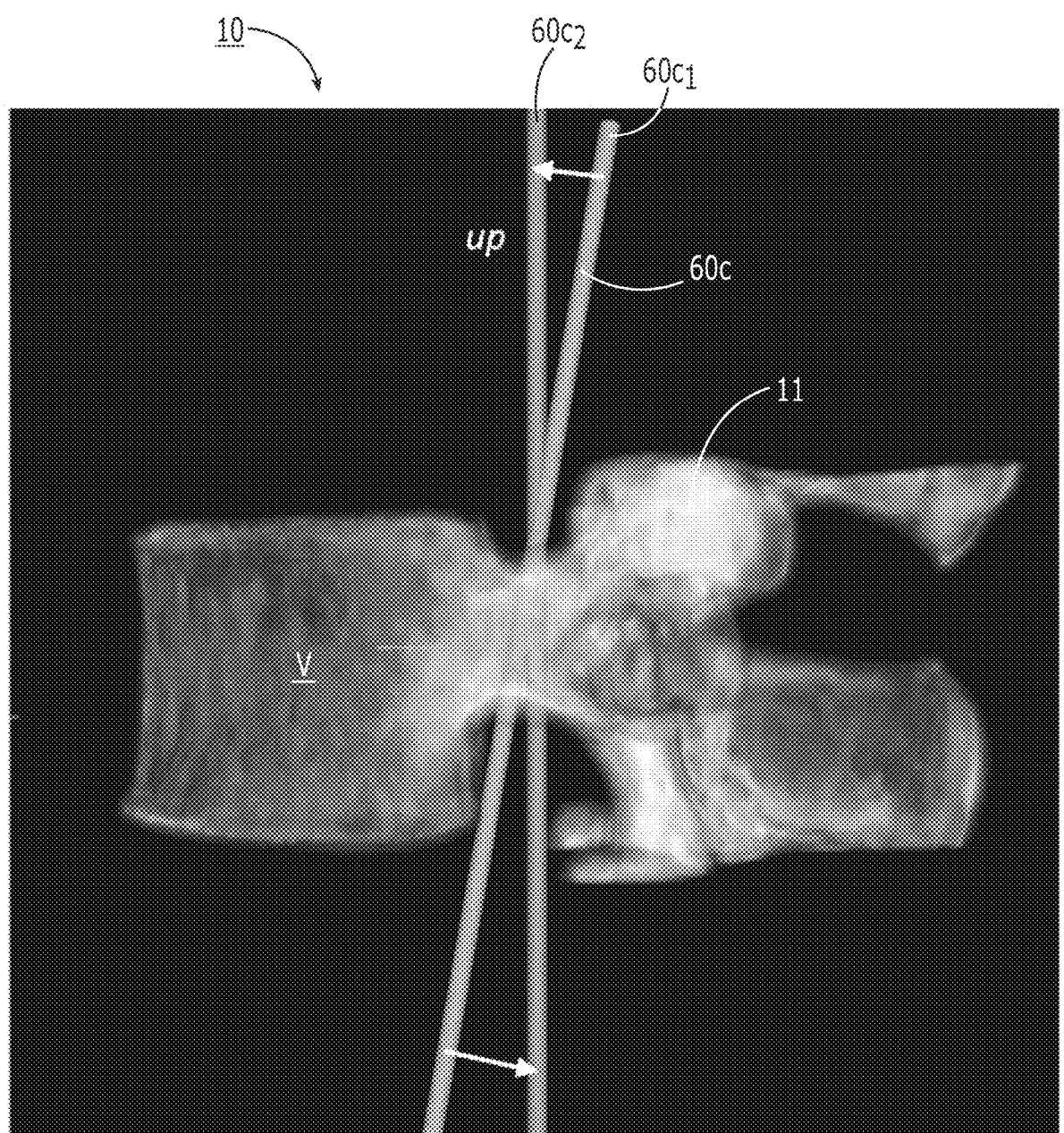
FIG. 4D illustrates the planning system with an adjusted VF centerline through relative to the centerline through the target vertebra shown in FIG. 4A according to embodiments of the present invention.

The VF centerline 60c, defined by the orientation and position of the matched cylindrical shape, can be used for generating a new coordinate system 200. Referring to FIG. 4D, the centerline direction from the VF centerline 60c calculation is used to define a refined up direction. The VF centerline 60c can be tilted forward a defined angle from the first orientation $60c_1$ to be a new adjusted centerline $60c_2$, i.e., rotate it around left. The tilt can be between 1-15 degrees, such as about 10 degrees, and may vary by patient and vertebra level. This action can cancel out the small tilt that most vertebrae VF have compared to the overall body anatomy. The system 10 can electronically store the result as up (i.e., the new local z-axis).

Figure 5:
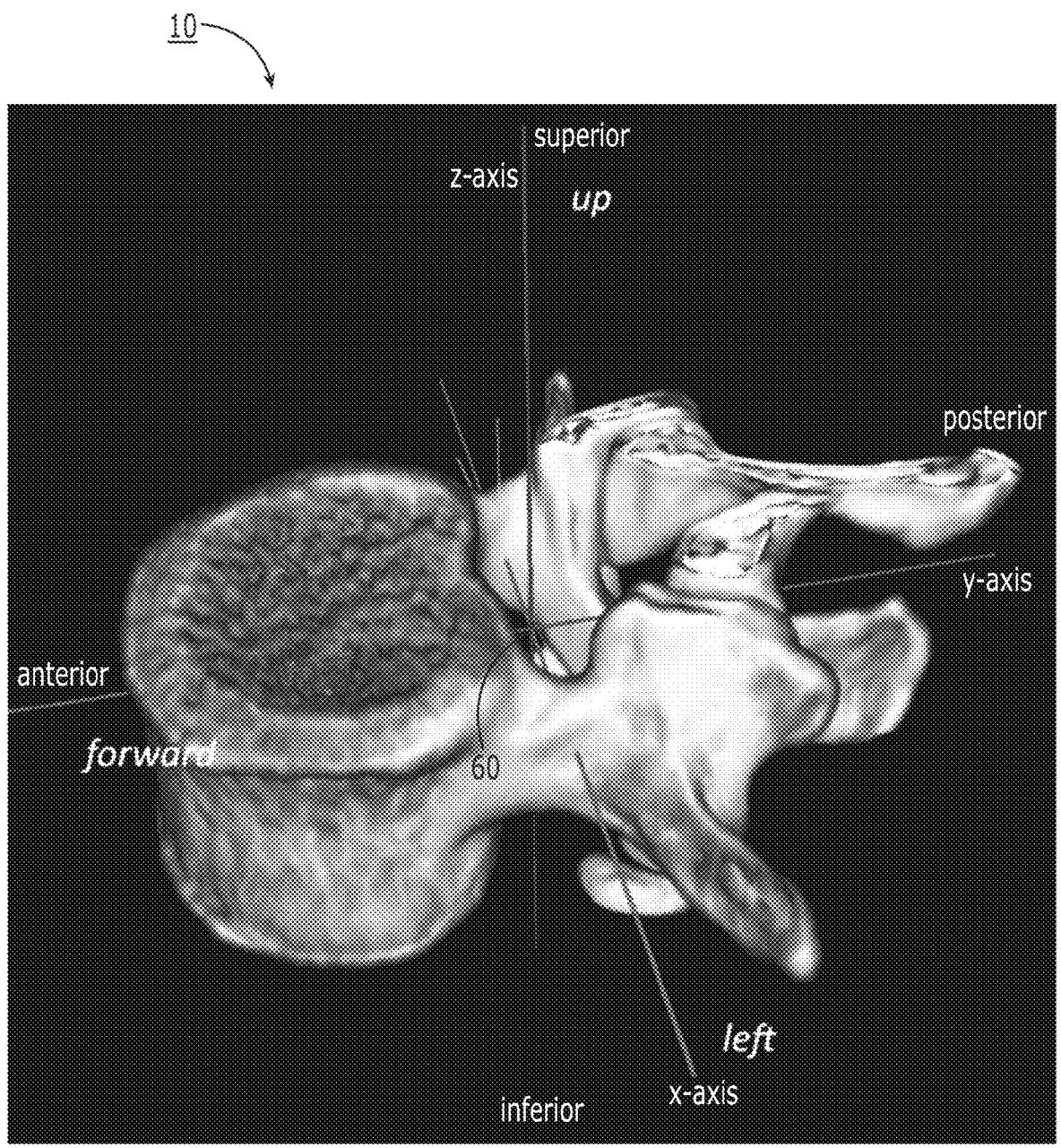
FIG. 5 illustrates the planning system with a new coordinate system using the location of the VF centerline according to embodiments of the present invention.

Referring to FIG. 5, the new coordinate system includes the new z-axis, and the forward parameter associated with the y-axis is calculated by the cross product of left and up. The left parameter associated with the x-axis is calculated by the cross product of forward and up.

Figure 6:
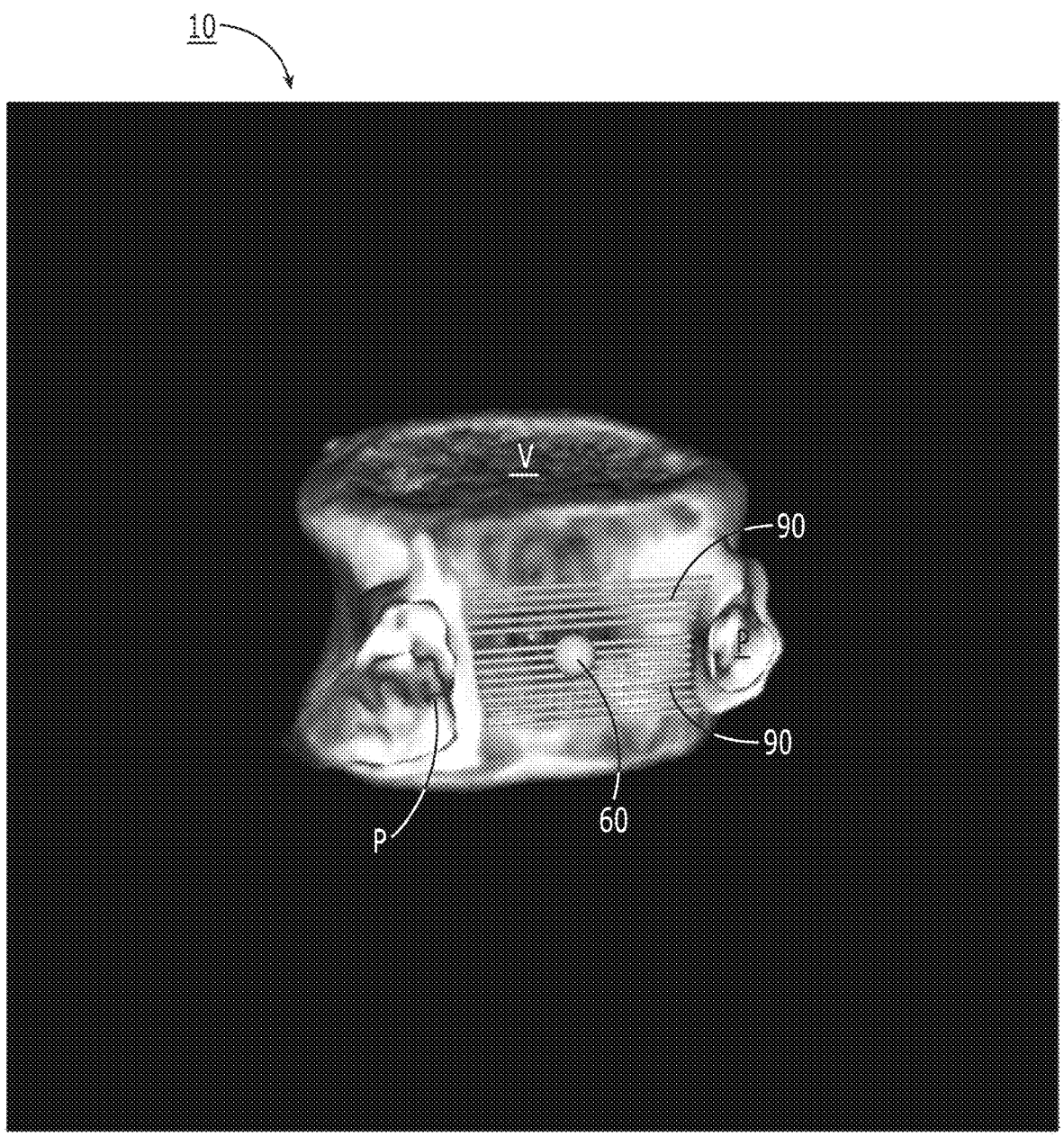
FIG. 6 illustrates the planning system adjusting the holeMid up or down (i.e., a height adjustment) to be between the center of the two pedicles of the target vertebra according to embodiments of the present invention.

Referring to FIG. 6, the system 10 can adjust holeMid 60 up and down to be between the center of the two pedicles P. From holeMid 60, step upwards and downwards (up and -up) with defined increments of between 0.1 mm and 2 mm, typically about 1 mm increments and store as center Up and centerDown. From each upward and downward point, ray cast left and right (left and -left) and store the rays 90 with bone hits. Repeat this process until the rays 90 do not hit anything or the distance between the hits is significantly longer, such as 50% longer, than the initial distance. This means that the pedicles P have been passed.

The system 10 can calculate the average between all or substantially all center Up and centerDown points to get the new height adjusted holeMid 60. The term "substantially all" for these points refers to at least 80% of these points.

Figure 7:
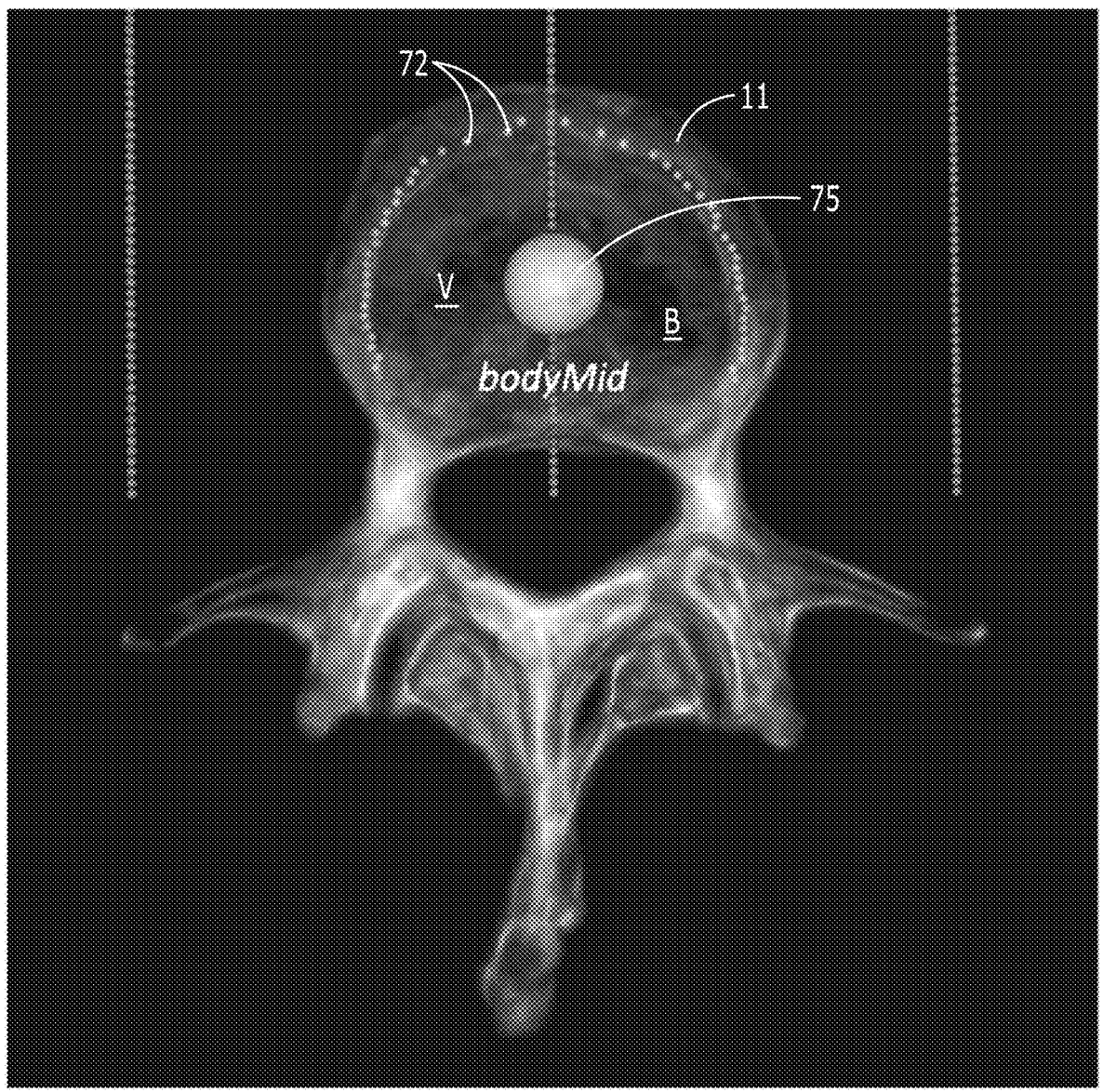
FIG. 7 illustrates the planning system electronically identifying a center or medial location of the vertebral body (bodyMid) according to embodiments of the present invention.

Referring to FIG. 7, up gives a good description of the vertebra tilt along x- and y-axis, but potentially not its rotation around the z-axis. The planning system 10 can find this by deriving the middle of the vertebral body B (bodyMid 75). Starting at midHole 60, the system 10 can electronically step along forward (the anterior direction of the y-axis) in defined increments, such as between 0.1 mm and 2 mm increments, typically about 1 mm increments. At each point p, shoot a plurality of rays, typically four rays:

two rays out from the point in left and right direction (outward from the inside of the vertebra) and two rays towards the point, starting at 40 mm left (p+left*40) and 40 mm right (p−left*40), respectively, (inwards from the outside of the vertebra). Hits can be registered (only) when a ray encounters cortical bone. If the two hits are registered on the one side (left or right), they can be merged into one average hit. Vice versa on the right side. The resulting points 72 will lie close to the surface of the vertebral body. The average of (all) points 72 can be used to define the middle of the body, bodyMid 75. The system 10 can update the forward direction associated with the y-axis to be the normalized vector (bodyMid−holeMid). The system can update the left direction associated with the x-axis by calculating the cross product of forward and up.

Referring to FIGS. 8A and 8B, the planning system 10 can then calculate a desired (i.e., optimal) placement for pedicle screws 30. A first set of points where the screws should pass, pedL and pedR, can be defined as follows. The most medial position for both pedicles P (the surface of the VF) can be found by ray casting along left and -left directions from holeMid 60, looking for cortical bone in the 3D image 11. Relative to the bone intersection points of the rays, pedL and pedR can be defined by points at a certain distance further along the respective ray, that is, further away from the VF. This distance should be slightly larger than the radius of the screw to use, for example, a distance between 0.5 mm to 5 mm larger than the radius, so that the screw will not intersect the VF.

The planning system 10 can find a front position, where the screws 30 will point towards. This position can be defined by bodyMid+(bodyMid−holeMid)*1.5.

As shown in FIGS. 8A and 8B, the system 10 can define two lines, from pedL to front and from pedR to front. For each line, where ped represents pedL and pedR respectively, the system can:
  i. Shoot a ray from front in the negative line direction (towards ped) and register the bone intersection point as frontHit
  ii. Shoot a ray from a point along the line to the back of the vertebra, given by ped+(ped−front), in the positive line direction and register the bone intersection point as backHit.
  iii. Place a virtual screw so that the position of the screw is backHit and the tip of the screw is at backHit+ (frontHit−backHit)*0.9

Figure 9A:
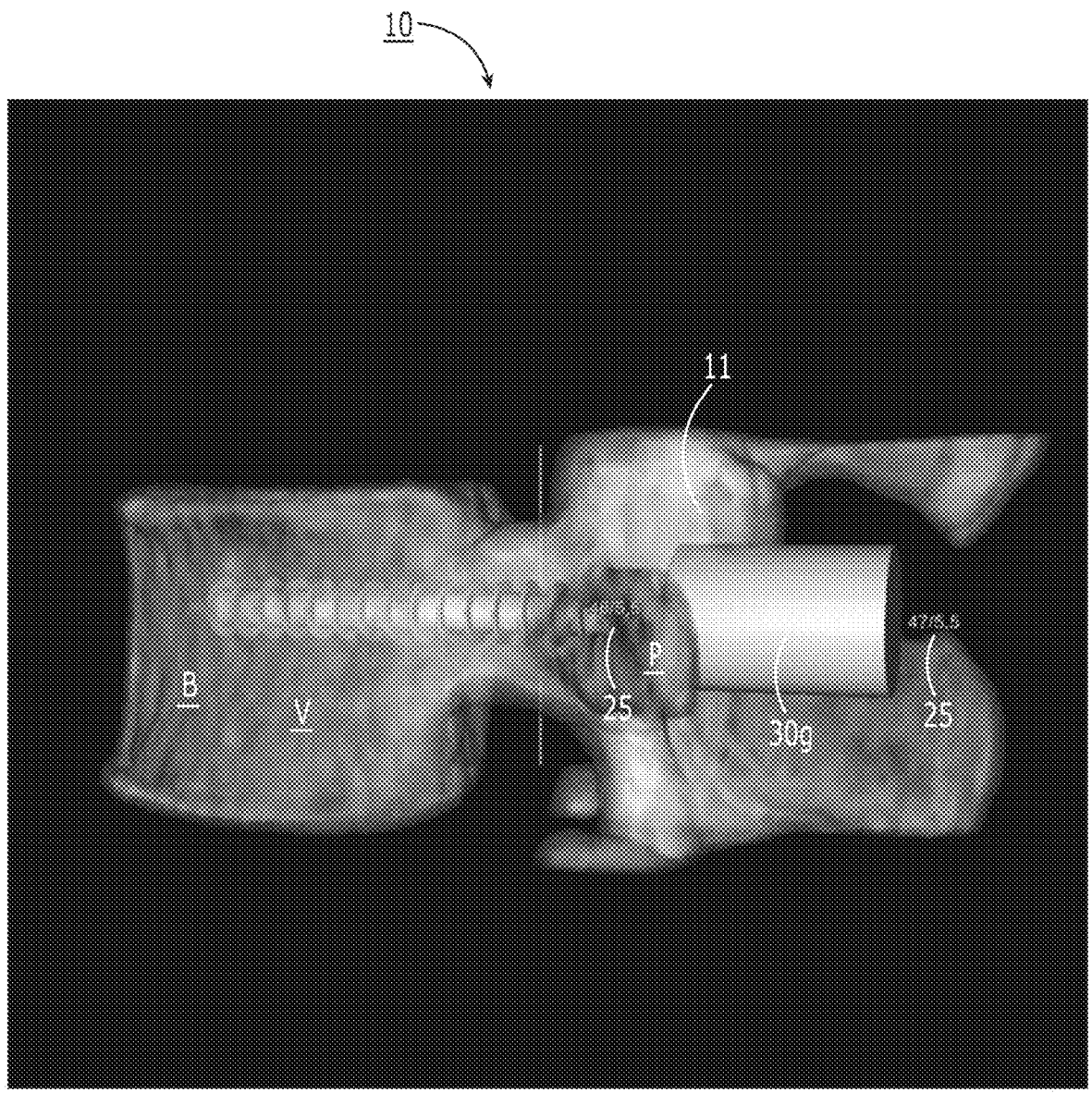
FIG. 9A and FIG. 9B illustrate the planning system showing an enlarged view of the target vertebra and a graphical representation of the pedicle screws with associated sizing information of each pedicle screw according to embodiments of the present invention.
Figure 9B:
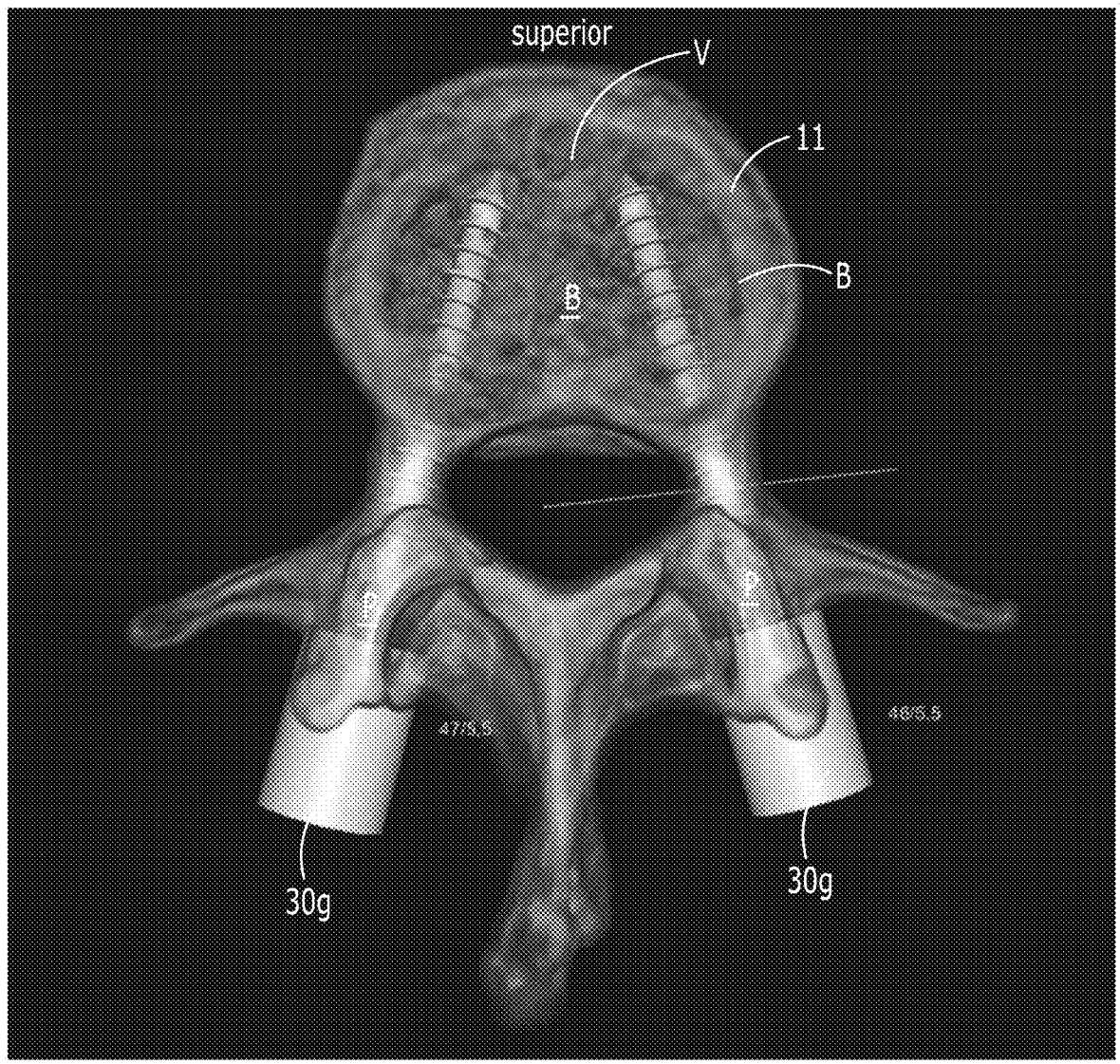

FIG. 9A and FIG. 9B illustrate a graphical representation 30g of the calculated proper placement of the pedicle screws 30 in the 3D medical image of the target vertebra V. As shown, the graphical representation 25 of a desired position, trajectory and insertion site can be visualized with appended sizing information 26 of the pedicle screws 30. Each screw 30 can have a different diameter size, length, head and trajectory from the pedicle to the vertebral body B.

Subsequent to the electronically calculated/given screw positioning, the user of the system can manually adjust the system-defined screw placement. To simplify the manual adjustment, the system can set the rotation center for the screw at the derived point ped, simplifying the manual adjustment to which angle the screw should be directed.

The automated pedicle placement planning system 10 can take the form of an entirely software embodiment or an embodiment combining software and hardware aspects, all generally referred to herein as a "circuit" 10c or "module" 10m (FIG. 2A). Furthermore, the present invention may take the form of a computer program product on a computer-usable storage medium having computer-usable program code embodied in the medium. Any suitable computer readable medium may be utilized including hard disks, CD-ROMs, optical storage devices, a transmission media such as those supporting the Internet or an intranet, or magnetic storage devices. Some circuits, modules or routines may be written in assembly language or even micro-code to enhance performance and/or memory usage. It will be further appreciated that the functionality of any or all of the program modules may also be implemented using discrete hardware components, one or more application specific integrated circuits (ASICs), or a programmed digital signal processor or microcontroller. Embodiments of the present invention are not limited to a particular programming language.

Computer program code for carrying out operations of data processing systems, method steps or actions, modules or circuits (or portions thereof) discussed herein may be written in a high-level programming language, such as Python, Java, AJAX (Asynchronous JavaScript), C, and/or C++, for development convenience. In addition, computer program code for carrying out operations of exemplary embodiments may also be written in other programming languages, such as, but not limited to, interpreted languages. Some modules or routines may be written in assembly language or even micro-code to enhance performance and/or memory usage. However, embodiments are not limited to a particular programming language. As noted above, the functionality of any or all of the program modules may also be implemented using discrete hardware components, one or more application specific integrated circuits (ASICs), or a programmed digital signal processor or microcontroller. The program code may execute entirely on one (e.g., a workstation computer), partly on one computer, as a stand-alone software package, partly on the workstation's computer or Scanner's computer and partly on another computer, local and/or remote or entirely on the other local or remote computer. In the latter scenario, the other local or remote computer may be connected to the user's computer through a local area network (LAN) or a wide area network (WAN), or the connection may be made to an external computer (for example, through the Internet using an Internet Service Provider).

The present invention is described in part with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing some or all of the functions/acts specified in the flowchart and/or block diagram block or blocks.

The flowcharts and block diagrams of certain of the figures herein illustrate exemplary architecture, functionality, and operation of possible implementations of embodiments of the present invention. In this regard, each block in the flow charts or block diagrams represents a module, segment, or portion of code, which comprises one or more executable instructions for implementing the specified logical function(s). It should also be noted that in some alternative implementations, the functions noted in the blocks may occur out of the order noted in the figures. For example, two blocks shown in succession may in fact be executed substantially concurrently or the blocks may sometimes be executed in the reverse order or two or more blocks may be combined, depending upon the functionality involved.

Figure 10:
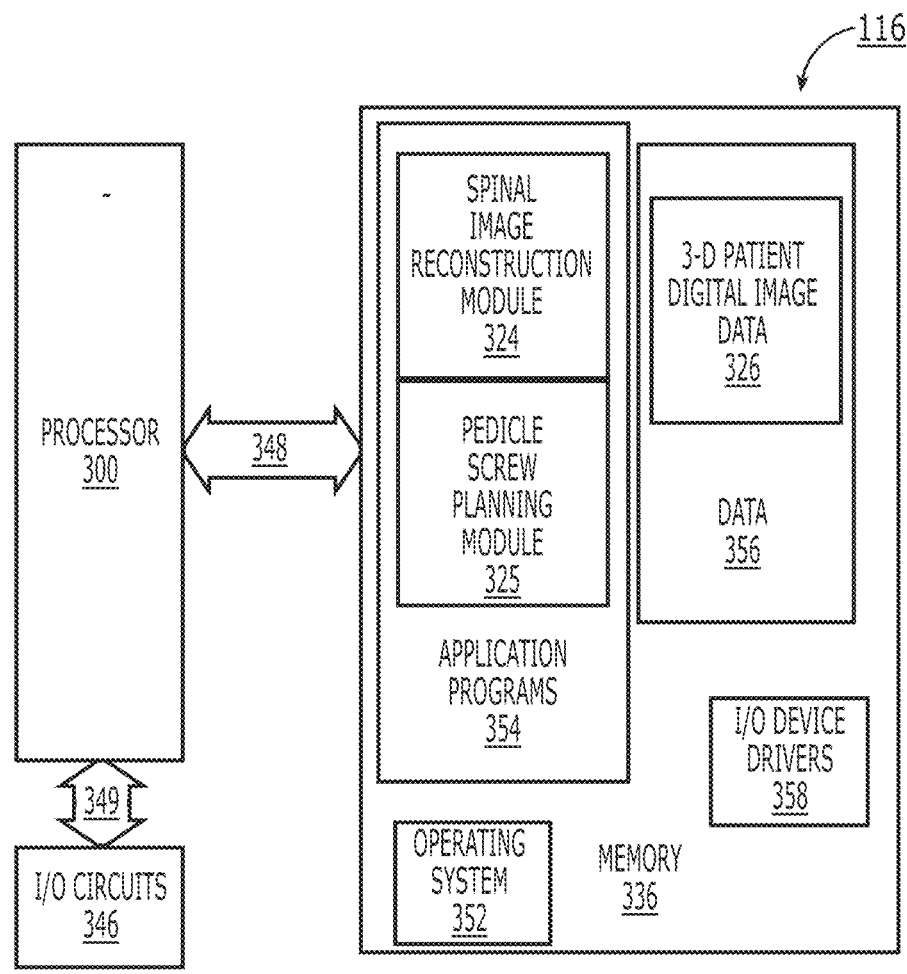
FIG. 10 is a block diagram of a data processing system according to embodiments of the present invention.

As illustrated in FIG. 10, embodiments of the invention may be configured as a data processing system 116, which can be used to carry out or direct operations of the planning system 10, and can include a processor 300, a memory 336 and input/output circuits 346. The data processing system may be incorporated in, for example, one or more of a personal computer, workstation W (FIGS. 2A and 2B), server(s) or the like. The system 116 can reside on one machine or be distributed over a plurality of machines and/or be a cloud based system. The processor 300 communicates with the memory 336 via an address/data bus 348 and communicates with the input/output circuits 346 via an address/data bus 349. The input/output circuits 346 can be used to transfer information between the memory (memory and/or storage media) 336 and another computer system or a network using, for example, an Internet protocol (IP) connection. These components may be conventional components such as those used in many conventional data processing systems, which may be configured to operate as described herein.

In particular, the processor 300 can be commercially available or custom microprocessor, microcontroller, digital signal processor or the like. The memory 336 may include any memory devices and/or storage media containing the software and data used to implement the functionality circuits or modules used in accordance with embodiments of the present invention. The memory 336 can include, but is not limited to, the following types of devices: ROM, PROM, EPROM, EEPROM, flash memory, SRAM, DRAM and magnetic disk. In some embodiments of the present invention, the memory 336 may be a content addressable memory (CAM).

As further illustrated in FIG. 10, the memory (and/or storage media) 336 may include several categories of software and data used in the data processing system: an operating system 352; application programs 354; input/output device drivers 358; and data 356. As will be appreciated by those of skill in the art, the operating system 352 may be any operating system suitable for use with a data processing system, such as IBM®, AIX® or zOS® operating systems or Microsoft® Windows2000 or WindowsXP operating systems, Windows Visa, Windows7, Windows CE or other Windows versions from Microsoft Corporation, Redmond, Wash., Palm OS, Symbian OS, Cisco IOS, VxWorks, Unix or Linux™, Mac OS from Apple Computer, LabView, or proprietary operating systems. IBM, AIX and zOS are trademarks of International Business Machines Corporation in the United States, other countries, or both while Linux is a trademark of Linus Torvalds in the United States, other countries, or both. Microsoft and Windows are trademarks of Microsoft Corporation in the United States, other countries, or both. The input/output device drivers 358 typically include software routines accessed through the operating system 352 by the application programs 354 to communicate with devices such as the input/output circuits 346 and certain memory 336 components. The application programs 354 are illustrative of the programs that implement the various features of the circuits and modules according to some embodiments of the present invention. Finally, the data 356 represents the static and dynamic data used by the application programs 354 the operating system 352 the input/output device drivers 358 and other software programs that may reside in the memory 336.

The data 356 may include (near real time or archived or stored) digital image data sets 326 that provides stacks of image data including meta data regarding, for example, voxel size (DICOM data to correlate the image data to respective patients). As further illustrated in FIG. 10, according to some embodiments of the present invention application programs 354 include a 3-D Image Reconstruction Module 324 and a Pedicle Screw Placement Planning Module 325. The application program 354 may be located in a local server (or processor) and/or database or a remote server (or processor) and/or database, or combinations of local and remote databases and/or servers.

While the present invention is illustrated with reference to the application programs 354, and Modules 324, 325 in FIG. 10, as will be appreciated by those of skill in the art, other configurations fall within the scope of the present invention. For example, rather than being application programs 354 these circuits and modules may also be incorporated into the operating system 352 or other such logical division of the data processing system. Furthermore, while the application programs 324, 325 are illustrated in a single data processing system, as will be appreciated by those of skill in the art, such functionality may be distributed across one or more data processing systems in, for example, the type of client/server arrangement described above. Thus, the present invention should not be construed as limited to the configurations illustrated in FIG. 10 but may be provided by other arrangements and/or divisions of functions between data processing systems. For example, although FIG. 10 is illustrated as having various circuits and modules, one or more of these circuits or modules may be combined or separated without departing from the scope of the present invention.

Figure 11:
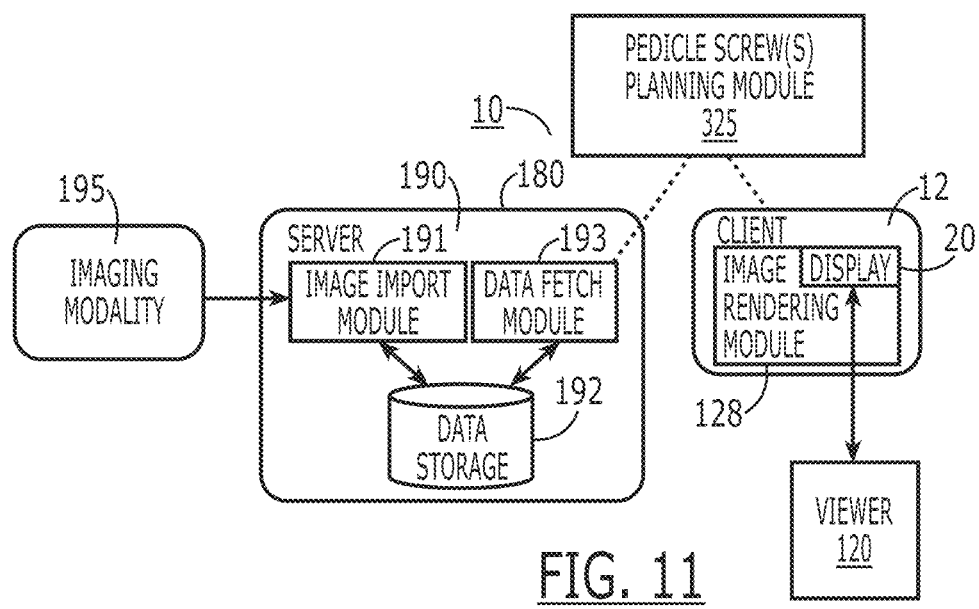
FIG. 11 is a schematic illustration of a surgical planning system for providing the pedicle screw placement and sizing information according to embodiments of the present invention.

FIG. 11 illustrates that, in particular embodiments, the planning system 10 can include or be in communication with a PACS (picture archiving and communication) system 180. The system 10 can include, for example, at least one server 190 with an image import module 191, data storage 192, and a data fetch module 193. The system 10 can include at least one (clinical) client (e.g., workstation) 12 and a rendering module 128. The system 10 can include a pedicle screw placement planning module 325. The module 325 can be in communication with the server 190, held partially or totally on one or more servers, or held partially or totally onboard the workstation 12. The module 325 can be provided as sub modules that are distributed over different servers or clients or may be provided as sub modules or subroutines on a respective server 190 or client associated with workstation 12. The system 10 can optionally be in communication with at least one imaging modality 195 that electronically obtains respective volume data sets (which for medical uses is patient data sets) and can electronically transfer the data sets to the electronic storage 192.

The at least one server 190 can be provided using cloud computing which includes the provision of computational resources on demand via a computer network. The resources can be embodied as various infrastructure services (e.g., compute, storage, etc.) as well as applications, databases, file services, email, etc. In the traditional model of computing, both data and software are typically fully contained on the user's computer; in cloud computing, the user's computer may contain little software or data (perhaps an operating system and/or web browser), and may serve as little more than a display terminal for processes occurring on a network of external computers. A cloud computing service (or an aggregation of multiple cloud resources) may be generally referred to as the "Cloud". Cloud storage may include a model of networked computer data storage where data is stored on multiple virtual servers, rather than being hosted on one or more dedicated servers.

A plurality of different clinical sites can be in communication with the server 190. The server 190 can receive and provide planning for multiple images of respective patients from the different sites at any one time.

In some particular embodiments, the imaging modality 195 can be any desirable modality such as, but not limited to MRI, CT (computed tomography), fluoroscopy, ultrasound, and the like. The system 10 may also operate to render images using data sets from more than one of these modalities. That is, the system 10 may be configured to render images irrespective of the imaging modality data type (i.e., a common system may render images for both CT and MRI volume image data). In some embodiments, the system 10 may optionally combine image data sets generated from different imaging modalities 195 to generate a combination image for a patient.

As shown, the system 10 can include at least one display 20, typically onboard or in communication with a clinical site workstation 12. As noted above, the display 20 can include a touch-input/touch-screen or click/mouse input with a GUI control 15. The display 20 may be held on any type display and, indeed, more than one display, including, for example, an electronic notebook, smart phone, laptop computer, desktop computer or a workstation 12.

Figure 12:
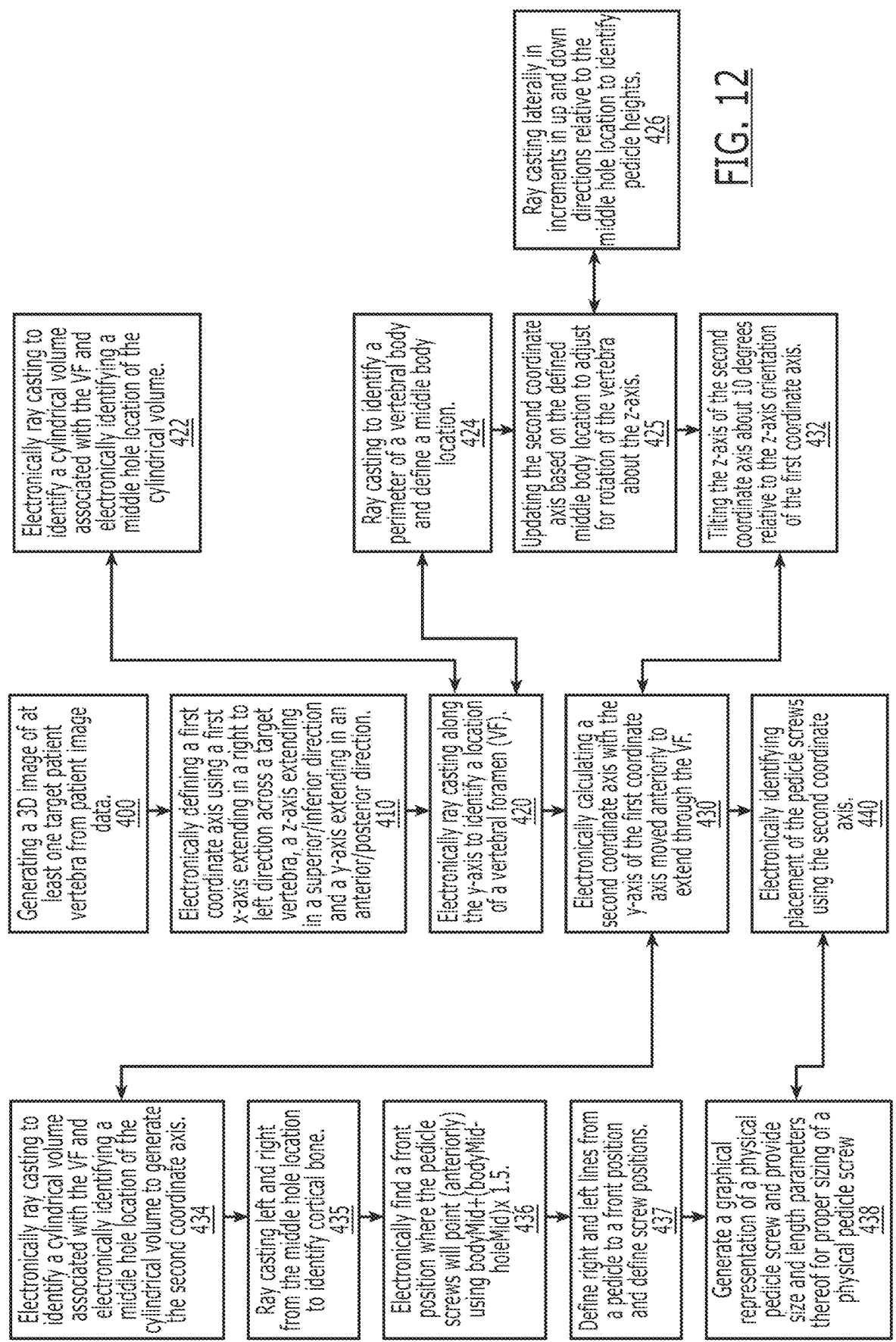
FIG. 12 is a flow chart of exemplary actions that can be used to carry out methods according to embodiments of the present invention.

Turning now to FIG. 12, a flow chart of exemplary operations that can be used to carry out embodiments of the invention is shown. A 3D image of at least one target patient vertebra is generated from patient image data (block 400). The 3D image can include one or more subvolumes of the patient image data set that can be electronically provided and reconstructed, with, a subvolume including at least one vertebrae (T1-L5). A first coordinate axis is electronically defined using a first x axis extending in a right to left direction across a target vertebra, a z-axis extending in a superior/inferior direction and a y-axis extending in an anterior/posterior direction (block 410). Optionally, the first x-axis can be generated based on user input of two spaced apart points in the x-axis direction on a posterior of the target vertebra. Electronically ray casting along the y-axis to identify a location of a vertebral foramen (VF) (block 420). Electronically calculating a second coordinate axis with the y-axis of the first coordinate axis moved anteriorly to extend through the VF (block 430). Electronically identifying placement of the pedicle screws using the second coordinate axis (block 440).

The methods can include electronically ray casting to identify a cylindrical volume associated with the VF and electronically identifying a middle hole location of the cylindrical volume (block 422).

The methods can include ray casting to identify a perimeter of a vertebral body and define a middle body location (block 424).

The methods can include updating the second coordinate axis based on the defined middle body location to thereby adjust for position (i.e., rotation) of the vertebra about the z-axis (block 425). The term "rotation" meaning adjustment around the z-axis, i.e., in a cw/ccw movement in the horizontal plane.

The methods can include tilting the z-axis of the second coordinate axis about 10 degrees relative to the z-axis orientation of the first coordinate axis (block 432).

The methods can include ray casting laterally (right to left direction) in increments in up and down directions relative to the middle hole location to identify pedicle heights (block 426).

The methods can include electronically ray casting to identify a cylindrical volume associated with the VF and electronically identifying a middle of the VF (midhole) location of the cylindrical volume to generate the second coordinate axis (block 434).

The methods can include ray casting left and right from the middle hole location to identify cortical bone (block 435).

The methods can include electronically fining a front position where the pedicle screws will point (anteriorly) using bodyMid+(bodyMid−holeMid)×1.5 (block 436).

The methods can include defining right and left lines from a pedicle to a front position and define screw positions (block 437).

The methods can include generating a graphical representation of a physical pedicle screw and provide size and length parameters thereof for proper sizing of a physical pedicle screw (block 438).

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

That which is claimed:

1. An automated or semi-automated method of planning for placement of pedicle screws, comprising:

providing a three dimensional (3D) image of a target vertebra of a patient;

electronically defining a first coordinate axis system using a first axis extending in an anatomical right to left direction across a target vertebra;

electronically ray casting the 3D image of the target vertebra in an anterior direction that is anterior to the first axis;

electronically identifying a vertebral foramen (VF) based at least in part on the ray casting;

electronically calculating a second coordinate axis system aligned with an orientation of the VF; and electronically identifying placement and sizing of at least one pedicle screw using the second coordinate axis system.

2. The method of claim 1, wherein the first and second coordinate systems are Cartesian coordinate systems, wherein the first axis is a first x-axis, a z-axis extends in a superior/inferior direction and a y-axis extends in an anterior/posterior direction.

3. The method of claim 1, wherein the ray casting identifies points on a boundary of bone tissue.

4. The method of claim 1, further comprising displaying the provided 3D image of the target vertebra, wherein the first x-axis is generated based on user input of first and second points, spaced apart in the right to left direction, on a posterior of the displayed target vertebra.

5. The method of claim 4, wherein the identifying the VF is carried out by: i) determining a midpoint between the first and second points from the user input, ii) for points along a line extending in the anterior direction from the midpoint, the electronically ray casting comprises applying a first ray casting that is carried out in the left and right directions to determine an intersection surface associated with bone tissue, iii) from the intersection surface, determining a point or points in an interior of the VF, and iv) from the interior point or points of the VF, applying a second ray casting to determine intersection points with the bone tissue that represent an inner surface of the VF.

6. The method of claim 5, wherein the step iv) second ray casting comprises spherically distributed ray casting to identify a point cloud having a cylindrical shape, and wherein the method further comprises electronically using the cylindrical shape to identify an orientation of the VF and a middle point of the VF.

7. The method of claim 6, wherein the second ray casting comprises casting rays in the left and right directions from regularly spaced apart points above and below the middle point of the VF, registering points until rays do not hit bone tissue within a distance of +/−50% of a radius of the cylindrical shape fitted to the VF, and adjusting the middle point of the VF along the z-axis to be an average of the z-axis position of the registered points.

8. The method of claim 6, wherein identifying the orientation of the VF is performed by electronically fitting a cylindrical model to the VF, comprising: approximating plane normals for each point neighborhood in the point cloud derived from the spherically distributed ray casting, fitting a plane to the collection of normal vectors which represents a cross-section of the cylinder, and using the normal of the cross-section plane to define a cylinder centerline direction of the cylinder.

9. The method of claim 5, further comprising electronically tilting the z-axis of the second coordinate axis system about 10 degrees in the anterior direction relative to an orientation in the first coordinate system then calculating an anatomical based orientation of the y-axis and x-axis of the second coordinate system based on the tilted z-axis.

10. The method of claim 1, further comprising electronically ray casting relative to a middle point of the VF in the second coordinate axis system to identify boundary points of cortical bone, then determining a perimeter of a vertebral body from the boundary points, calculating a middle body location of the vertebral body (bodyMid) spaced apart from and adjacent the VF, and updating the second coordinate axis system based on the defined middle body location to thereby adjust for rotation of the vertebra about the z-axis.

11. The method of claim 1, wherein the pedicle screw placement and sizing comprises determining a first control point left or right of a midpoint of the VF in the second coordinate axis system, the control point being adjacent to the VF and within bone tissue but sufficiently distant to the VF to prevent a properly placed and sized pedicle screw from penetrating the VF.

12. The method of claim 11, wherein the pedicle screw placement and sizing further comprises determining a second control point anterior to the vertebra, along the y-axis from the midpoint of the VF in the second coordinate axis system, and wherein the pedicle screw placement is defined by a line through the first and second control points.

13. The method of claim 11, further comprising allowing a manual adjustment of the electronically identified pedicle screw placement, wherein the first control point is set to be a fixed center of rotation for a user for the manual adjustment of the pedicle screw placement.

14. The method of claim 1, further comprising:
electronically ray casting the target vertebra from a point in the middle of the VF (holeMid) to identify a perimeter of a vertebral body;
electronically calculating a middle body location of the vertebral body (bodyMid);
electronically ray casting the target vertebra laterally in a right to left direction in increments in up and down directions relative to holeMid to identify pedicle heights;
electronically defining a front/anterior position where the pedicle screws will point using the equation: bodyMid+ (bodyMid−holeMid)×1.5;
electronically defining right and left lines of a trajectory of respective right and left pedicle screws from a pedicle to a front position;
generating a graphical representation of physical pedicle screws with the graphical representation placing the pedicle screws perpendicular to the cylinder shape in an anterior direction from the pedicles; and
electronically providing size and length parameters of right and left physical pedicle screws as the electronically identifying the placement and sizing.

15. The method of claim 14, further comprising:
determining the intersection points of vertebra boundary along a pedicle screw trajectory at the front and back of the vertebra, and determining the size of the pedicle screw as a predefined proportion of the distance between the intersection points.

16. The method of claim 1, wherein the electronically identifying placement and sizing of one or two pedicle screws for a single vertebra is carried out in between 100 and 200 milliseconds.

17. A clinician workstation comprising:
at least one display; and
a circuit in communication with the at least one display, the circuit comprising or in communication with at least one processor configured to:
provide a three dimensional (3D) image of a target vertebra of a patient;
define a first coordinate axis system using a first axis extending in an anatomical right to left direction across a target vertebra;
ray cast the 3D image of the target vertebra in an anterior direction that is anterior to the first axis;
identify a vertebral foramen (VF) based at least in part on the ray casting;
calculate a second coordinate axis system aligned with an orientation of the VF; and
identify placement and sizing of at least one pedicle screw using the second coordinate axis system.

18. The workstation of claim 17, wherein the circuit with the at least one processor directs the display to display the provided 3D image of the target vertebra, and accepts user input of first and second points spaced apart in the right to left direction, on a posterior of the displayed target vertebra, and wherein the first x-axis is generated based on the user input.

19. The workstation of claim 18, wherein the VF is identified by: i) determining a midpoint between the first and second points from the user input, ii) for points along a line extending in the anterior direction from the midpoint, the electronically ray casting comprises applying a first ray casting that is carried out in the left and right directions to determine an intersection surface associated with bone tissue, iii) from the intersection surface, determining a point or points in an interior of the VF, and iv) from the interior point or points of the VF, applying a second ray casting to determine intersection points with the bone tissue that represent an inner surface of the VF.

20. The workstation of claim 17, wherein the identification of the pedicle screw placement and sizing comprises determining a first control point left or right of a midpoint of the VF in the second coordinate axis system, the control point being adjacent to the VF and within bone tissue but sufficiently distant to the VF to prevent a properly placed and sized pedicle screw from penetrating the VF.

21. The workstation of claim 20, wherein the identification of the pedicle screw placement and sizing further comprises determining a second control point anterior to the vertebra, along the y-axis from the midpoint of the VF in the second coordinate axis system, and wherein the pedicle screw placement is defined by a line through the first and second control points.

22. A system for evaluating 3-D spinal patient image data for pedicle placement planning, comprising:
    a pedicle placement planning module comprising at least one processor; and
    at least one display in communication with the pedicle placement planning module comprising the at least one processor,
    wherein the pedicle planning placement module is configured to carry out the method of claim 1.

* * * * *

UNITED STATES PATENT AND TRADEMARK OFFICE
CERTIFICATE OF CORRECTION

PATENT NO. : 10,561,466 B2
APPLICATION NO. : 16/046181
DATED : February 18, 2020
INVENTOR(S) : Hedblom et al.

Page 1 of 1

It is certified that error appears in the above-identified patent and that said Letters Patent is hereby corrected as shown below:

In the Specification

Column 2, Line 53: Please correct "+1-50%" to read -- +/-50% --

Signed and Sealed this
Sixteenth Day of June, 2020

Andrei Iancu
*Director of the United States Patent and Trademark Office*